(12) United States Patent
Johnson et al.

(10) Patent No.: US 6,485,504 B1
(45) Date of Patent: Nov. 26, 2002

(54) HARD OR SOFT TISSUE CLOSURE

(75) Inventors: Greg A. Johnson, Pittsburgh, PA (US); James F. Antaki, Allison Park, PA (US); James A. Magovern, 603 Twin Pine Rd., Pittsburgh, PA (US) 15215; Matthew R. Frushell, Gibsonia, PA (US); Thomas David Will, Liberty Boro, PA (US); John Andrew Holmes, Wexford, PA (US)

(73) Assignee: James A. Magovern, Pittsburgh, PA (US)

( * ) Notice: Subject to any disclaimer, the term of this patent is extended or adjusted under 35 U.S.C. 154(b) by 32 days.

(21) Appl. No.: 09/599,775

(22) Filed: Jun. 22, 2000

(51) Int. Cl.[7] ............................................. A61B 17/04
(52) U.S. Cl. ...................... 606/216; 606/72; 606/233
(58) Field of Search ........................ 606/72, 104, 215, 606/216, 233, 152; 289/2, 17

(56) References Cited

U.S. PATENT DOCUMENTS

| | | | | |
|---|---|---|---|---|
| 3,103,218 A | * | 9/1963 | Ajemian | 24/265 R |
| 3,625,220 A | * | 12/1971 | Engelsher | 285/303 |
| 3,648,705 A | * | 3/1972 | Lary | 606/233 |
| 3,845,772 A | * | 11/1974 | Smith | 606/232 |
| 4,210,148 A | * | 7/1980 | Stivala | 606/232 |
| 5,921,986 A | * | 7/1999 | Bonutti | 606/215 |
| 5,989,252 A | * | 11/1999 | Fumex | 606/72 |

* cited by examiner

*Primary Examiner*—Gary Jackson
(74) *Attorney, Agent, or Firm*—Ansel M. Schwartz

(57) ABSTRACT

An apparatus for holding a first portion of a bone and a second portion of a bone together for the bone to heal. A method for holding a first portion of a bone and a second portion of a bone together for the bone to heal. A suture. A grommet for a bone. A method for securing a suture through a bone.

12 Claims, 16 Drawing Sheets

HARD OR SOFT TISSUE CLOSURE

FIELD OF THE INVENTION

The present invention is related to the closure of hard or soft tissue that has been separated. More specifically, the present invention is related to the closure of a sternum with the use of wire sutures inserted through grommets or sleeves and placed into the sternum.

BACKGROUND OF THE INVENTION

There are various circumstances in which separated tissue of a patient needs to be brought together so it can heal. Tissue is defined as bone, muscle or fascia that has been divided to gain access the thoracic cavity, mediastinum, or abdomen. For instance, in chest surgery, many times the sternum is separated so a surgeon can again gain access to the chest cavity and organs, muscle and tissue therein. After the surgeon has finished his procedure regarding the chest cavity, the sternum needs to be closed. Key to the healing process of the sternum is the proper stabilization and contact of the two severed sides together. Heretofore, there have been many techniques used to bring the separated sides of the sternum together and maintain them in contact so the healing process can occur. However, these techniques generally limit the movement the patient can experience without damaging or affecting the healing sternum. Furthermore, the process of introducing tools to bring the separated sides of the sternum together can itself create risk or cause damage to the sternum.

The present invention provides for bringing the separate sides of the sternum together while minimizing damage to them and maintaining them while also allowing some flexibility and movement by the patient without disturbing the healing process.

SUMMARY OF THE INVENTION

The present invention pertains to an apparatus for holding a first portion of a bone and a second portion of a bone together for the bone to heal. The apparatus comprises a first bendable hollow sleeve adapted for insertion into the first portion of the bone. The apparatus comprises a second bendable hollow sleeve adapted for insertion into a second portion of the bone. The apparatus comprises a suture which is threaded through the first and second sleeves. The apparatus comprises a pusher for pushing the first and second sleeves into the first and second portions of the bone, respectively, wherein when the suture is tightened, the first and second portions are pulled together and the first and second sleeves bend and protect the first and second portions from the suture.

The present invention pertains to a method for holding a first portion of a bone and a second portion of a bone together for the bone to heal. The method comprises the steps of inserting a first bendable hollow sleeve into the first portion of the bone. Then there is the step of inserting a second bendable hollow sleeve into the second portion of the bone. Next there is the step of threading a suture through the first and second sleeves. Then there is the step of pulling the first portion and second portion together with the suture and causing the first and second sleeves to bend and protect the first and second portions from the suture contacting the first and second portions.

The present invention pertains to an apparatus for holding a first portion of a bone and a second portion of a bone together for the bone to heal. The apparatus comprises a first bendable hollow sleeve adapted for insertion into the first portion of the bone. The first sleeve having a cap adapted to seat on a top surface of the first portion. The apparatus comprises a second bendable hollow sleeve adapted for insertion into a second portion of the bone, the second sleeve having a cap adapted to seat on a top surface of the second portion. The apparatus comprises a suture which is threaded through the first and second sleeves.

The present invention pertains to an apparatus for holding a first portion of a bone and a second portion of a bone together for the bone to heal. The apparatus comprises a first bendable hollow sleeve adapted for insertion into the first portion of the bone. The apparatus comprises a second bendable hollow sleeve adapted for insertion into a second portion of the bone. The apparatus comprises a suture which is threaded through the first and second sleeves. The apparatus comprises an implantor which holds the first or second sleeve and inserts the first or second sleeve into the first or second portion, respectively.

The present invention pertains to an apparatus for holding a first portion of a bone and a second portion of a bone together for the bone to heal. The apparatus comprises a hollow tube adapted to extend from the first and second portions. The apparatus comprises a suture which is adapted to extend through the hollow tube when the hollow tube extends through the first and second portion. The apparatus comprises a first bottom cap and second bottom cap disposed on the suture and adapted to fit in the bottom of the first and second portion, respectively. The apparatus comprises a first top cap and second top cap through which the suture is inserted when the tube is removed. The first and second cap is adapted to fit in the top of the first and second portions, respectively.

The present invention pertains to a method for holding a first portion of a bone and a second portion of a bone together for the bone to heal. The method comprises the steps of inserting a first end of a hollow tube into the top surface of the first portion, through the first portion and out the bottom of the first portion. Then there is the step of inserting a second end of the hollow tube into the top surface of the second portion, through the second portion and out the bottom of the second portion. Next there is the step of inserting a first end of the suture having a first bottom cap and second bottom cap on the suture into the first end of the hollow tube until it extends past the top surface of the first portion. Then there is the step of inserting a second end of the suture having the first bottom cap and second bottom cap on the suture into the second end of the hollow tube until it extends past the top surface of the second portion. Next there is the step of removing the tube from the suture and the first and second portion. Then there is the step of sliding the first bottom cap along the suture to the bottom surface of the first portion. Next there is the step of placing the first bottom cap into the bottom surface of the first portion. Then there is the step of sliding the second bottom cap along the suture to the bottom surface of the second portion. Next there is the step of placing the second bottom cap into the bottom surface of the second portion. Then there is the step of placing a first top cap over the first end of the suture and into the top surface of the first portion. Next there is the step of placing a second top cap over the second end of the suture and into the top surface of the second portion. Then there is the step of moving the first portion and second portion together. Next there is the step of closing the first end and second end of the suture together to hold the first portion and second portion together.

The present invention pertains to a suture. The suture comprises a wire adapted to extend through bone of a patient. The suture comprises an insulation portion disposed about the wire and adapted to protect the bone from the wire.

The present invention pertains to a method for holding a first portion of a bone and a second portion of a bone together for the bone to heal. The method comprises the steps of extending a suture comprising a wire and an insulation portion about the wire through the first portion and the second portion. Then there is the step of pulling the first portion and second portion together. Next there is the step of securing the first and second portions together with the suture wherein the insulation of the suture protects the first portion and second portion from the wire.

The present invention pertains to a grommet for a bone. The apparatus comprises a top cap having a top flange that is adapted to seat on the top surface of the bone and a threaded portion which extends from the top flange and is adapted to be disposed in the bone, the top flange and threaded portion having a top channel extending through them. The apparatus comprises a bottom cap having a bottom flange that is adapted to seat on the bottom surface of the bone and a bottom strut which extends from the bottom portion and engages with the threaded portion to hold the top cap to the bottom cap and is adapted to be disposed in the bone, the bottom flange and a strut having a bottom channel extending through them, the top channel and bottom channel adapted for a suture to extend through the top channel and bottom channel.

The present invention pertains to a method for securing a suture through a bone. The method comprises the steps of placing a bottom cap of a grommet into the bone wherein a bottom flange of the bottom cap seats on the bottom surface of the bone and a bottom strut of the bottom cap connecting to the bottom flange extends into the bone. Then there is the step of placing a top cap of a grommet into the bone wherein the top flange of the top cap seats on the top surface of the bone and a threaded portion of the top cap is connected to the top flange and extends into the bone and contacts the bottom strut. Next there is the step of screwing the threaded portion of the top cap into the bottom strut. Then there is the step of passing a suture through the bone via a channel of the top cap and bottom cap.

The present invention pertains to an apparatus for holding together a first portion of a bone and a second portion of a bone for the bone to heal. The apparatus comprises a wire having a first end and a second end. The apparatus comprises a first needle attached to the first end. The apparatus comprises a second needle attached to the second end. The apparatus comprises a first bottom cap with a flange adapted for placement into the bottom of the first portion with the wire through it. The apparatus comprises a second bottom cap with a flange adapted for placement into the bottom of the second portion with the wire through it. The apparatus comprises a first top cap with a flange adapted for placement into the top of the first portion with the wire through it. The apparatus comprises a second top cap with a flange adapted for placement into the top of the second portion with the wire through it.

The present invention pertains to a method for holding a first portion of a bone and a second portion of a bone together for the bone to heal. The method comprises the steps of passing a first needle attached to a first end of a suture through the first portion. Then there is the step of passing a second needle attached to a second end of a suture through the second portion. Next there is the step of guiding a first bottom cap through which the suture is disposed along the suture until it contacts the first portion. Then there is the step of inserting the first bottom cap into the bottom of the first portion. Next there is the step of guiding a second bottom cap through which the suture is disposed along the suture until it contacts the second portion. Then there is the step of inserting the second bottom cap into the bottom of the second portion. Next there is the step of separating the first needle from the first end. Then there is the step of separating the second needle from the second end. Next there is the step of passing the first end through a first top cap. Then there is the step of guiding the first top cap along the wire. Next there is the step of inserting the first top cap into the top surface of the first portion. Then there is the step of passing the second end through a second top cap. Next there is the step of guiding the second top cap along the wire. Then there is the step of inserting the second top cap into the top surface of the second portion. Next there is the step of securing the suture in place about the first and second portion by connecting the first and second ends.

The present invention pertains to an apparatus for holding a first portion of a bone and a second portion of a bone together for the bone to heal. The apparatus comprises a strap made of a memory metal having a central portion with a right side and a left side, a right portion that extends angularly downward from the central portion adjacent to the right portion, and a left portion that extends angularly downward from the central portion adjacent to the left side. The right and left portion is adapted to extend into and through the first and second portion of the one, respectively, with the central portion disposed along the top surface of the first and second portions. The bottom of the right and left portions curling and hooking into the first and second portions, respectively, to grip the first and second portions.

The present invention pertains to a method for holding a first portion of a bone and a second portion of a bone together for the bone to heal. The method comprises the steps of inserting a right portion of a strap made of a memory metal into and through the first portion of the bone and a left portion of the strap into and through the second portion of the bone with a central portion of the strap connecting the right portion and the left portion and extending over and between the first and second portions. Then there is the step of heating the right portion and left portion until they curl and the bottom of the right and left portions hook into the first and second portions, respectively.

The present invention pertains to an apparatus for holding a first portion of a bone and a second portion of a bone together for the bone to heal. The apparatus comprises a plurality of grommets, each grommet having a channel, a flange adapted to seat on the surface of the bone, and a tube which extends from the flange and is adapted to be disposed in the bone. The apparatus comprises a suture which extends through at least two of the plurality of grommets which oppose each other when they are disposed in the first and second portions of the bone, respectively. The apparatus comprises a poker which removably fits in the channel of a grommet and has a pointed end adapted to pierce the bone and to install the grommet into the bone. The apparatus comprises a platform against which the tube of one of the grommets with the poker through it is pressed to cause the end of the tube to flare out and form a bottom flange that seats on the bottom surface of the bone.

The present invention pertains to an apparatus for holding a first portion of a bone and a second portion of a bone together for the bone to heal. The apparatus comprises a plurality of grommets, each having a channel and a top portion and a bottom portion, each portion having a flange adapted to seat on the surface of the bone, and a tube which extends from the flange and is adapted to be disposed in the bone. The apparatus comprises a poker which removably fits in the channel of the top and bottom portions and has a pointed end adapted to pierce the bone and to install the top portion into the bone and along which the bottom portion fits to be guided into the bottom of the bone.

The present invention pertains to a method for holding a first portion of a bone and a second portion of a bone together for the bone to heal. The method comprises the steps of placing a poker having a pointed end through a channel of a first grommet having a top flange and a tube which extends from the top flange. Then there is the step of inserting the poker, pointed end first, with the first grommet on it through the top surface of the first portion until it contacts a platform disposed adjacent the bottom surface of the first portion and the tube of the grommet is disposed in and extends through the first portion. Next there is the step of pressing the poker against the platform until the bottom of the tube flares out and forms a bottom flange. Then there is the step of removing the poker from the first grommet leaving the first grommet in the first portion with the top flange and bottom flange adjacent to the top surface and bottom surface, respectively. Next there is the step of implanting a second grommet having a channel in the second portion. Then there is the step of extending a suture through the channels of the first and second grommets. Next there is the step of bringing the first and second portions together. Then there is the step of securing the first and second portions together with the suture.

The present invention pertains to a method for holding a first portion of a bone and a second portion of a bone together for the bone to heal. The method comprises the steps of placing a poker having a pointed end through a channel of a top portion of a first grommet having a top flange and a tube which extends from the top flange. Then there is the step of inserting the poker, pointed end first, with the top portion of the first grommet on it through the top surface of the first wherein the flange seats on the top surface of the first portion and the tube is disposed in the first portion. Next there is the step of placing a tube of a bottom portion of the first grommet on the pointed end. Then there is the step of sliding the bottom portion along the poker until a flange of the bottom portion seats on the bottom surface of the first portion and the tube of the bottom portion is in the bottom of the first portion. Next there is the step of removing the poker from the first grommet leaving the first grommet in the first portion with the top flange and bottom flange seated on the top surface and bottom surface, respectively. Then there is the step of implanting a second grommet having a channel in the second portion. Next there is the step of extending a suture through the channels of the first and second grommets. Then there is the step of bringing the first and second portions together. Next there is the step of securing the first and second portions together with the suture.

The present invention pertains to a grommet for a bone. The grommet comprises a top cap having a top flange adapted for placement on the top surface of the bone and a top strut adapted for placement in the bone extending from the top flange, the top strut having slots disposed along its outer surface. The top cap having a channel for a suture to extend through. The top strut adapted for placement in the bone. The grommet comprises a bottom cap having a bottom flange adapted for placement on the bottom surface of the bone and a bottom strut adapted for placement in the bone extending from the bottom flange, the bottom strut having a catch extending from its inner surface to engage a slot to secure the top cap and bottom cap together.

The present invention pertains to a method for holding a first portion of a bone and a second portion of a bone together for the bone when to heal. The method comprises the steps of inserting a top strut of a top cap of a first grommet into a hole in the top surface of the first portion until a top flange of the top cap seats on the top surface of the bone. Then there is the step of inserting a bottom strut of a bottom cap of the first grommet into the hole in the bottom surface of the first portion until a catch extending from the inner surface of the bottom strut of engages a slot disposed along the outer surface of the top strut wherein the top cap and bottom cap are secured together. Next there is the step of inserting a second grommet having a channel into a second portion of the bone. Then there is the step of threading a suture through a channel of the first grommet and the channel of the second grommet. Next there is the step of pulling the first portion the second portion together. Then there is the step of securing the suture wherein the first portion and second portion are secured together.

The present invention pertains to a grommet for insertion in a bone. The grommet comprises a housing having a channel for a suture. The housing is adapted for placement in the bone. The housing has at least one pre-crimp in its wall which expands outward and collapses when the housing is compressed in an axial direction.

The present invention pertains to a method for placing a suture through a bone. The method comprises the steps of inserting a grommet into a bone. Then there is the step of compressing the grommet axially from its top and bottom causing a pre-crimp in the housing wall to extend outward and collapse to form an anchor in the bone. Next there is the step of threading a suture through a channel in the grommet.

The present invention pertains to a grommet for implantation into a hole in hard or soft tissue of a patient. The grommet comprises a spring having a head flange adapted to seat on the top portion of the tissue. The grommet comprises a tail flange adapted to seat on the top portion of the tissue. The grommet comprises an elongate central portion connected to the head flange and the tail flange.

BRIEF DESCRIPTION OF THE DRAWINGS

In the accompanying drawings, the preferred embodiment of the invention and preferred methods of practicing the invention are illustrated in which.

DETAILED DESCRIPTION

Figure 1:
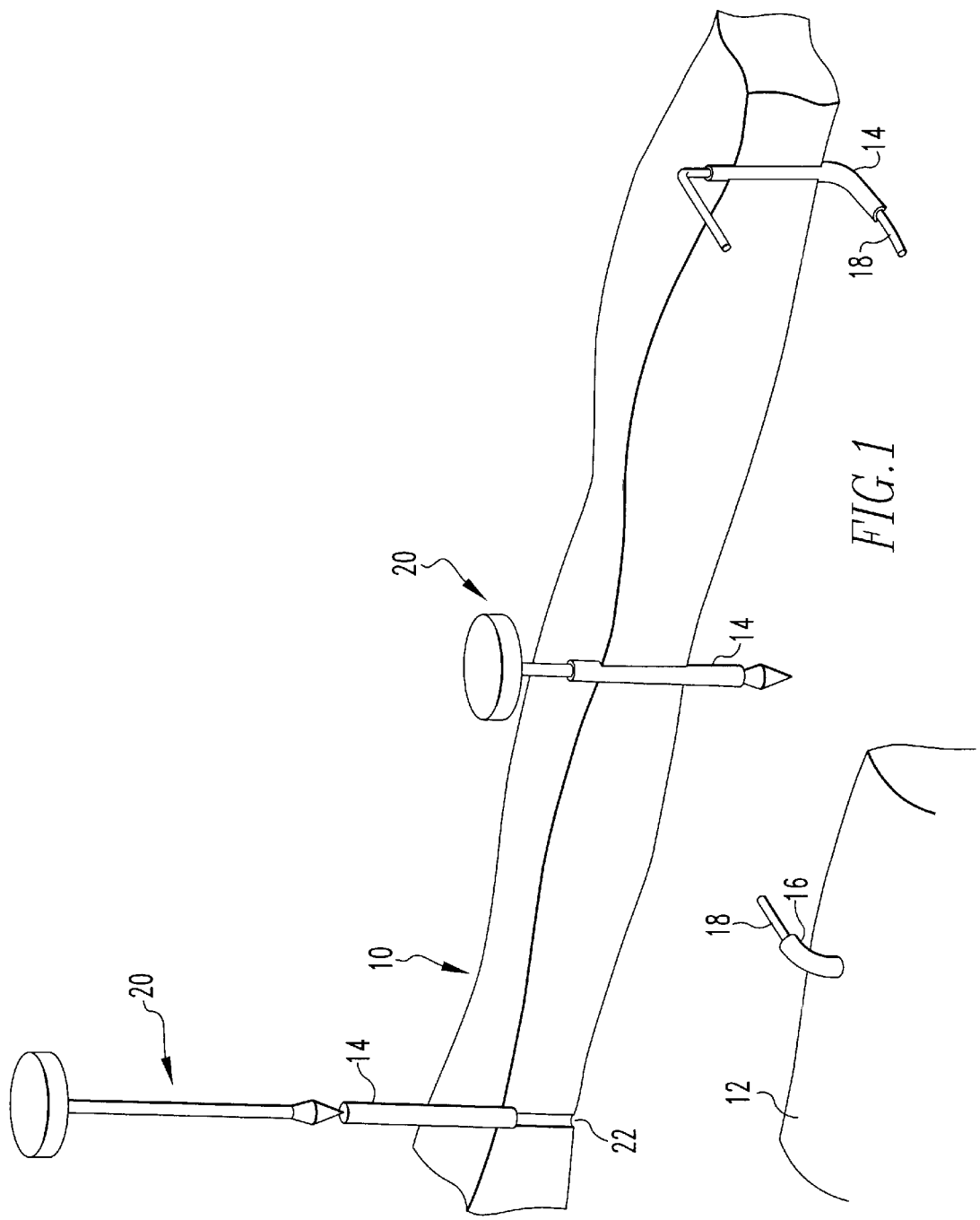
FIG. 1 is a schematic representation of a first embodiment of the present invention.

Referring now to the drawings wherein like reference numerals refer to similar or identical parts throughout the several views, and more specifically to FIG. 1 thereof, there is shown an apparatus for holding a first portion 10 of a bone and a second portion 12 of a bone together for the bone to heal. The apparatus comprises a first bendable hollow sleeve adapted for insertion into the first portion 10 of the bone. The apparatus comprises a second bendable hollow sleeve adapted for insertion into a second portion 12 of the bone. The apparatus comprises a suture 18 which is threaded through the first and second sleeves. The apparatus comprises a pusher 20 for pushing the first and second sleeves into the first and second portions 10, 12 of the bone, respectively, wherein when the suture 18 is tightened, the first and second portions 10, 12 are pulled together and the first and second sleeves bend and protect the first and second portions 10, 12 from the suture 18.

The present invention pertains to a method for holding a first portion 10 of a bone and a second portion 12 of a bone together for the bone to heal, as shown in FIG. 1. The method comprises the steps of inserting a first bendable hollow sleeve into the first portion 10 of the bone. Then there is the step of inserting a second bendable hollow sleeve into the second portion 12 of the bone. Next there is the step of threading a suture 18 through the first and second sleeves. Then there is the step of pulling the first portion 10 and second portion 12 together with the suture 18 and causing the first and second sleeves to bend and protect the first and second portions 10, 12 from the suture 18 contacting the first and second portions 10, 12.

Preferably, after the pulling step, there is the step of closing the first and second ends 48, 50 of the suture 18 together. The first sleeve inserting step includes the step of placing a pusher in the first sleeve, pushing the first sleeve through the first portion 10 with the pusher, and removing the pusher from the first sleeve.

Preferably, the second sleeve inserting step includes the step of placing the pusher in the second sleeve, pushing the second sleeve through the second portion 12 with the pusher, and removing the pusher from the second sleeve.

Before the inserting the first sleeve step, there is preferably the step of forming a hole 22 through the first portion 10. Preferably, before the inserting the second sleeve step, there is the step of forming a hole 22 through the second portion 12. After the first sleeve inserting step, there is the step of seating a cap of the first sleeve on the top surface 26 of the first portion 10 and after the second sleeve inserting step, there is the step of seating a cap of the second sleeve on a top surface 26 of the second portion 12, as shown in FIG. 4.

Figure 3:
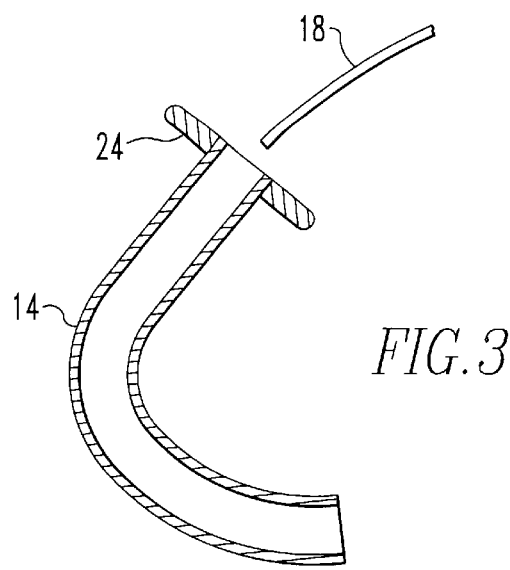
FIG. 3 is a schematic representation of another embodiment of the present invention.

The present invention pertains to an apparatus for holding a first portion 10 of a bone and a second portion 12 of a bone together for the bone to heal, as shown in FIG. 3. The apparatus comprises a first bendable hollow sleeve adapted for insertion into the first portion 10 of the bone. The first sleeve having a cap adapted to seat on a top surface 26 of the first portion 10. The apparatus comprises a second bendable hollow sleeve adapted for insertion into a second portion 12 of the bone. The second sleeve has a cap adapted to seat on a top surface 26 of the second portion 12. The apparatus comprises a suture 18 which is threaded through the first and second sleeves.

Alternatively, the inserting the first sleeve step includes the step of inserting an implantor 30 in which the first sleeve is disposed into the first portion 10 and wherein the inserting the second sleeve step includes the step of inserting the implantor 30 in which the second slave is disposed into the second portion 12. Before the first sleeve inserting step, there is preferably the step of placing the first sleeve with the implantor 30.

Figure 4:
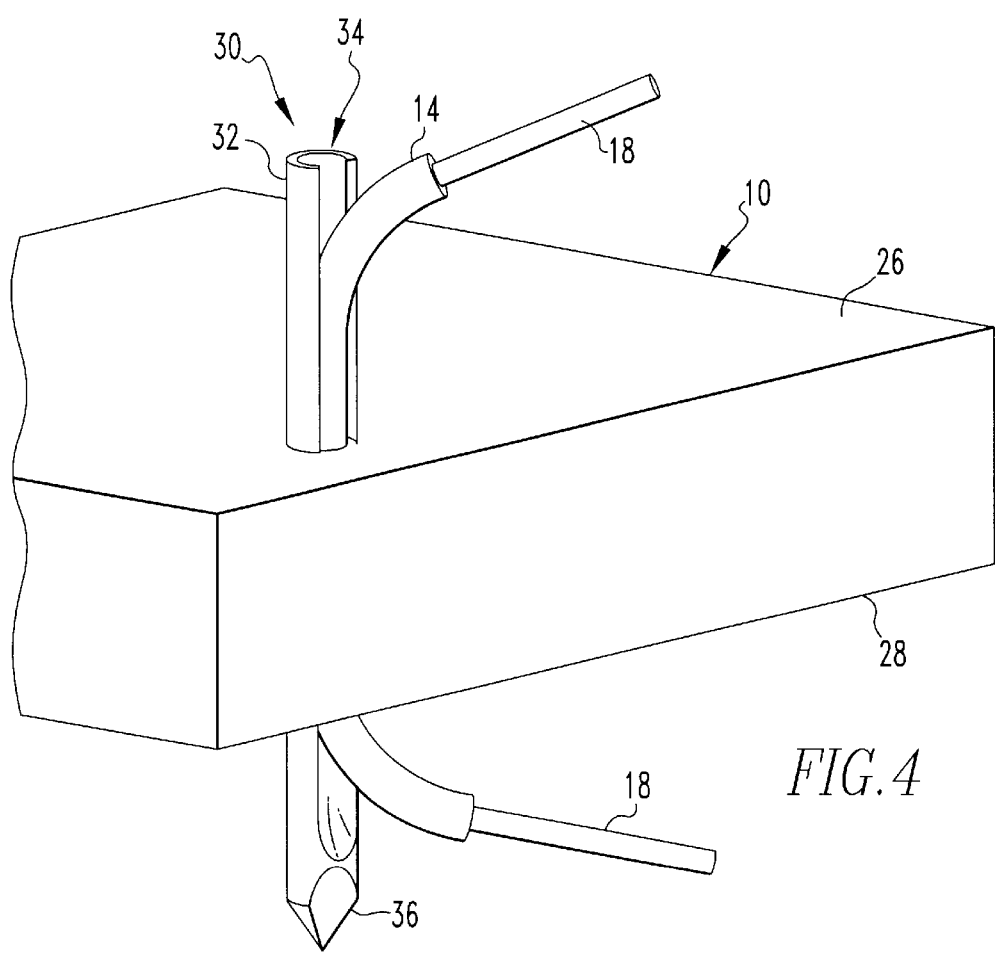
FIG. 4 is a schematic representation of another embodiment of the present invention.

The present invention pertains to an apparatus for holding a first portion 10 of a bone and a second portion 12 of a bone together for the bone to heal, as shown in FIG. 4. The apparatus comprises a first bendable hollow sleeve adapted for insertion into the first portion 10 of the bone. The apparatus comprises a second bendable hollow sleeve adapted for insertion into a second portion 12 of the bone. The apparatus comprises a suture 18 which is threaded through the first and second sleeves. The apparatus comprises an implantor 30 which holds the first or second sleeve and inserts the first or second sleeve into the first or second portion 10, 12, respectively.

Figure 5:
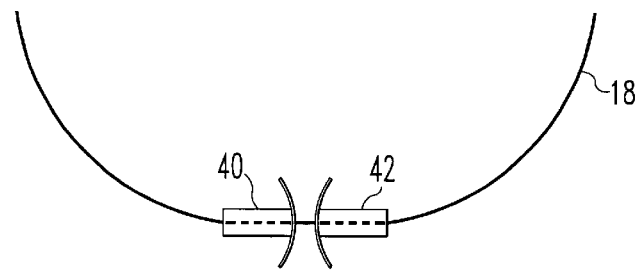
FIG. 5 is a schematic representation of a suture having a first bottom cap and a second bottom cap.
Figure 6:
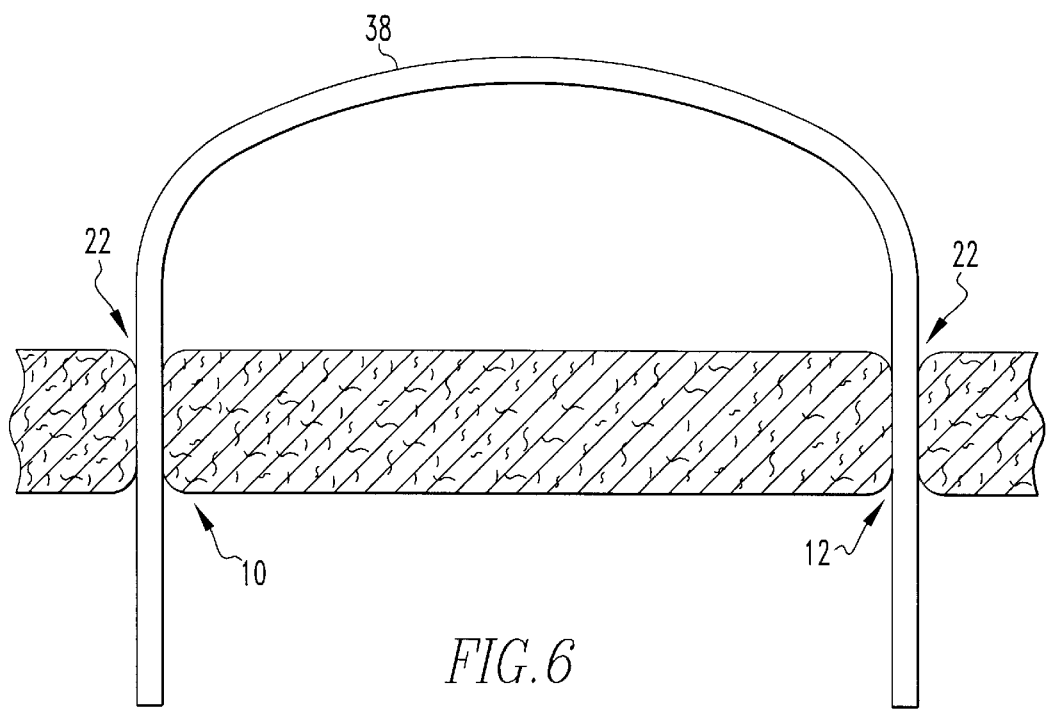
FIG. 6 is a schematic representation of the tube in a first portion and a second portion of a bone.
Figure 7:
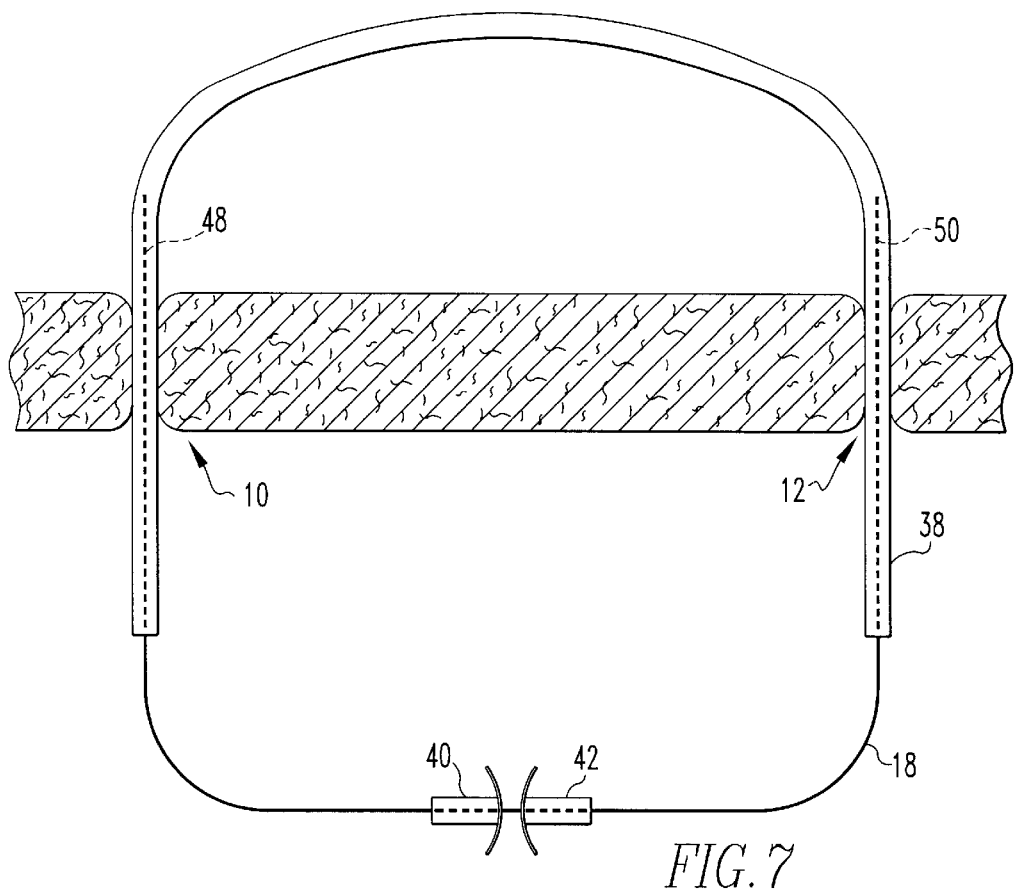
FIG. 7 is a schematic representation of another embodiment of the present invention.
Figure 8:
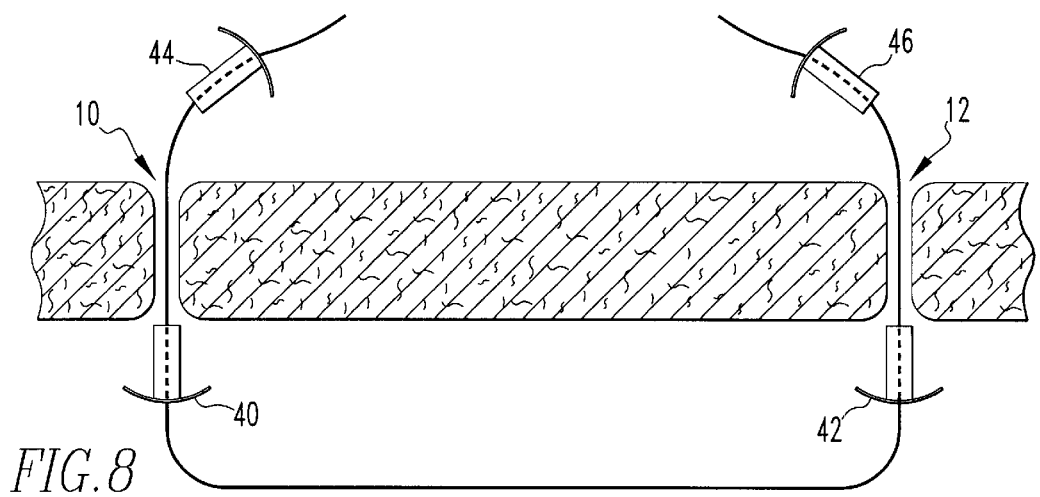
FIG. 8 is a schematic representation of the embodiment of FIG. 7 with the tube removed.
Figure 9:
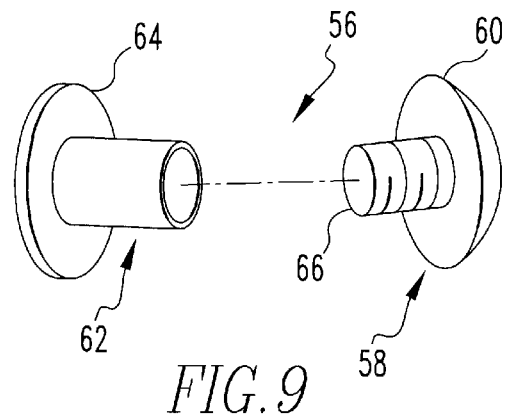
FIG. 9 is a schematic representation of a grommet which is separated.
Figure 10:
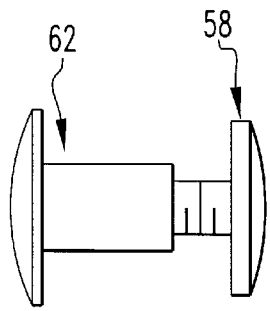
FIG. 10 is a schematic representation of a grommet intact.
Figure 11:
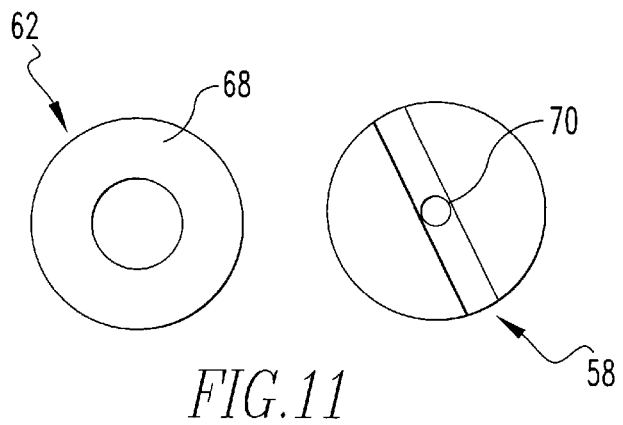
FIG. 11 is a schematic representation of a top view and bottom view of the grommet.

The present invention pertains to an apparatus for holding a first portion 10 of a bone and a second portion 12 of a bone together for the bone to heal, as shown in FIGS. 5, 6 and 7. The apparatus comprises a hollow tube 38 adapted to extend from the first and second portions 10, 12. The apparatus comprises a suture 18 which is adapted to extend through the hollow tube 38 when the hollow tube 38 extends through the first and second portions 10, 12. The apparatus comprises a first bottom cap 40 and second bottom cap 42 disposed on the suture 18 and adapted to fit in the bottom of the first and second portions 10, 12, respectively. The apparatus comprises a first top cap 44 and second top cap 46 through which the suture 18 is inserted when the tube is removed. The first and second cap is adapted to fit in the top of the first and second portions 10, 12, respectively. Preferably, the implantor 30 has a housing of a cylindrical shape with a groove 34 in which the first or second sleeve fits, and with a pointed end.

The present invention pertains to a method for holding a first portion 10 of a bone and a second portion 12 of a bone together for the bone to heal, as shown in FIGS. 5, 6 and 7. The method comprises the steps of inserting a first end of a hollow tube 38 into the top surface 26 of the first portion 10, through the first portion 10 and out the bottom of the first portion 10. Then there is the step of inserting a second end 50 of the hollow tube 38 into the top surface 26 of the second portion 12, through the second portion 12 and out the bottom of the second portion 12. Next there is the step of inserting a first end of the suture 18 having a first bottom cap 40 and second bottom cap 42 on the suture 18 into the first end of the hollow tube 38 until it extends past the top surface 26 of the first portion 10. Then there is the step of inserting a second end 50 of the suture 18 having the first bottom cap 40 and second bottom cap 42 on the suture 18 into the second end 50 of the hollow tube 38 until it extends past the top surface 26 of the second portion 12. Next there is the step of removing the tube from the suture 18 and the first and second portions 10, 12. Then there is the step of sliding the first bottom cap along the suture 18 to the bottom surface of the first portion 10. Next there is the step of placing the first bottom cap into the bottom surface of the first portion 10. Then there is the step of sliding the second bottom cap 42 along the suture 18 to the bottom surface of the second portion 12. Next there is the step of placing the second bottom cap 42 into the bottom surface of the second portion 12. Then there is the step of placing a first top cap 44 over the first end of the suture 18 and into the top surface 26 of the first portion 10. Next there is the step of placing a second top cap 46 over the second end 50 of the suture 18 and into the top surface 26 of the second portion 12. Then there is the step of moving the first portion 10 and second portion 12 together. Next there is the step of closing the first end 48 and second end 50 of the suture 18 together to hold the first portion 10 and second portion 12 together.

Figure 2:
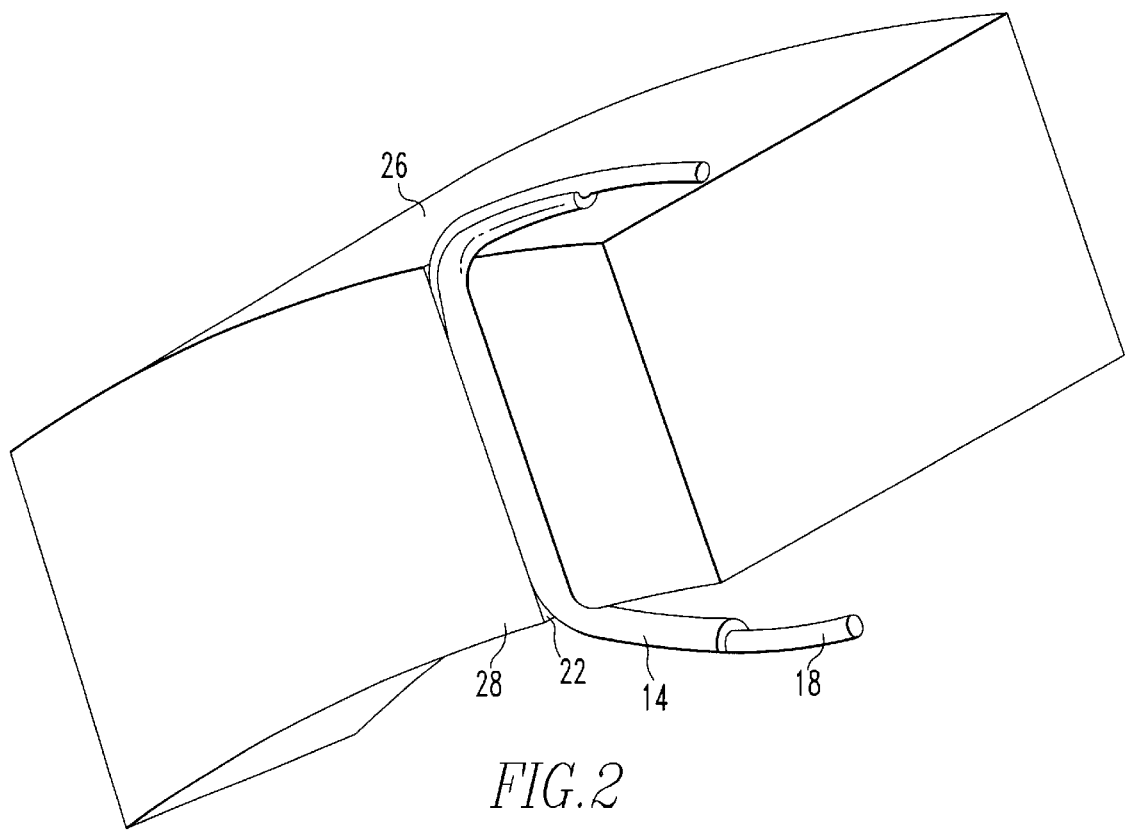
FIG. 2 is a schematic representation of a suture in a sleeve and a first portion of bone.

The present invention pertains to a suture 18, as shown in FIG. 2. The suture 18 comprises a wire adapted to extend through bone of a patient. The suture 18 comprises an insulation 54 portion disposed about the wire and adapted to protect the bone from the wire.

The present invention pertains to a method for holding a first portion 10 of a bone and a second portion 12 of a bone together for the bone to heal, as shown in FIG. 2. The method comprises the steps of extending a suture 18 comprising a wire and an insulation 54 portion about the wire through the first portion 10 and the second portion 12. Then there is the step of pulling the first portion 10 and second portion 12 together. Next there is the step of securing the first and second portions 10, 12 together with the suture 18 wherein the insulation 54 of the suture 18 protects the first portion 10 and second portion 12 from the wire.

The present invention pertains to a grommet for a bone, as shown in FIGS. 9–11 and 13. The apparatus comprises a top cap having a top flange 60 that is adapted to seat on the top surface 26 of the bone and a threaded portion which extends from the top flange 60 and is adapted to be disposed in the bone, the top flange 60 and threaded portion having a top channel 70 extending through them. The apparatus comprises a bottom cap 62 having a bottom flange that is adapted to seat on the bottom surface of the bone and a bottom strut 66 which extends from the bottom portion and engages with the threaded portion to hold the top cap to the bottom cap 62 and is adapted to be disposed in the bone, the bottom flange and a strut 66 having a bottom channel extending through them, the top channel 70 and bottom channel adapted for a suture 18 to extend through the top channel 70 and bottom channel.

The present invention pertains to a method for securing a suture 18 through a bone, as shown in FIGS. 9–11 and 13. The method comprises the steps of placing a bottom cap 62 of a grommet into the bone wherein a bottom flange of the bottom cap 62 seats on the bottom surface of the bone and a bottom strut 66 of the bottom cap 62 connecting to the bottom flange extends into the bone. Then there is the step of placing a top cap of a grommet into the bone wherein the top flange 60 of the top cap seats on the top surface 26 of the bone and a threaded portion of the top cap is connected to the top flange 60 and extends into the bone and contacts the bottom strut 66. Next there is the step of screwing the threaded portion of the top cap into the bottom strut 66. Then there is the 10 step of passing a suture 18 through the bone via a channel of the top cap 58 and bottom cap 62.

Figure 12:
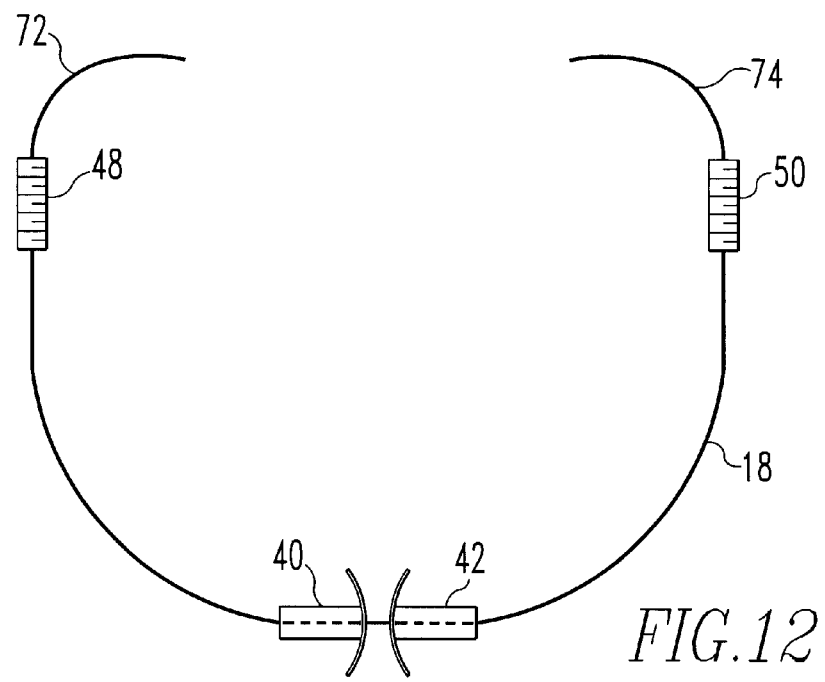
FIG. 12 is a schematic representation of another embodiment of the present invention.

The present invention pertains to an apparatus for holding together a first portion 10 of a bone and a second portion 12 of a bone for the bone to heal, as shown in FIG. 12. The apparatus comprises a wire having a first end 48 and a second end 50. The apparatus comprises a first needle attached to the first end. The apparatus comprises a second needle 74 attached to the second end 50. The apparatus comprises a first bottom cap 40 with a flange adapted for placement into the bottom of the first portion 10 with the wire through it. The apparatus comprises a second bottom cap 42 with a flange adapted for placement into the bottom of the second portion 12 with the wire through it. The apparatus comprises a first top cap 44 with a flange adapted for placement into the top of the first portion 10 with the wire through it. The apparatus comprises a second top cap 46 with a flange adapted for placement into the top of the second portion 12 with the wire through it.

The present invention pertains to a method for holding a first portion 10 of a bone. and a second portion 12 of a bone together for the bone to heal, as shown in FIG. 12. The method comprises the steps of passing a first needle attached to a first end of a suture 18 through the first portion 10. Then there is the step of passing a second needle 74 attached to a second end 50 of a suture 18 through the second portion 12. Next there is the step of guiding a first bottom cap 40 through which the suture 18 is disposed along the suture 18 until it contacts the first portion 10. Then there is the step of inserting the first bottom cap 40 into the bottom of the first portion 10. Next there is the step of guiding a second bottom cap 42, through which the suture 18 is disposed along the suture 18 until it contacts the second portion 12. Then there is the step of inserting the second bottom cap 42. into the,bottom of the second portion 12. Next there is the step of separating the first needle from the first end. Then there is the step of separating the second needle 74 from the second end 50. Next there is the step of passing the first end through a first top cap 44. Then there is the step of guiding the first top cap 44 along the wire. Next there is the step of inserting the first top cap 44 into the top surface 26 of the first portion 10. Then there is the step of passing the second end 50 through a second top cap 46. Next there is the step. of guiding the second top cap 46 along the wire. Then there is the step of inserting the second top cap 46 into the top surface 26 of the second portion 12. Next there is the step of securing the suture 18 in place about the first and second portions 10, 12 by connecting the first and second ends 48, 50.

Figure 14:
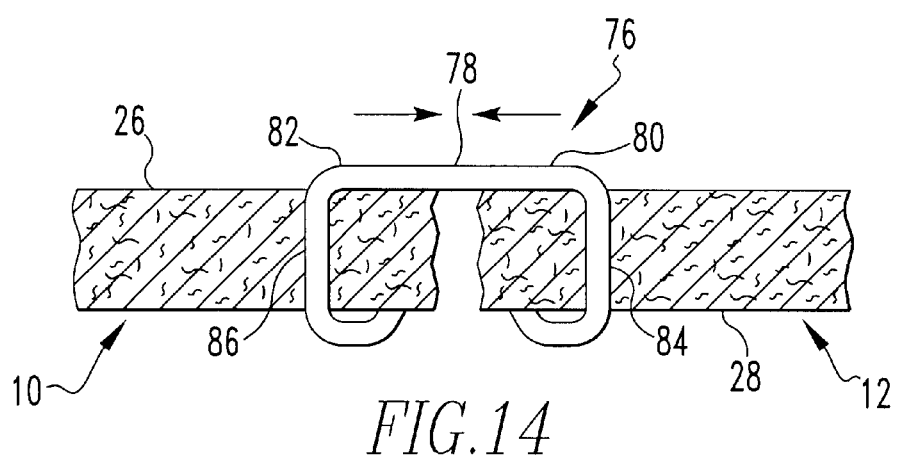
FIG. 14 is a schematic representation of a strap disposed in a first portion and second portion of bone.
Figure 13:
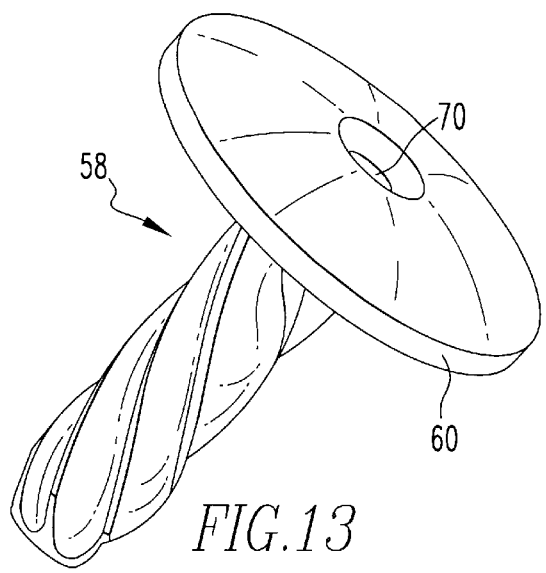
FIG. 13 is a schematic representation of a top cap.

The present invention pertains to an apparatus for holding a first portion 10 of a bone and a second portion 12 of a bone together for the bone to heal, as shown in FIG. 14. The apparatus comprises a strap made of a memory metal having a central portion 78 with a right side 80 and a left side 82, a right portion 84 that extends angularly downward from the central portion 78 adjacent to the right portion 84, and a left portion that extends angularly downward from the central portion 78 adjacent to the left side 82. The right and left portion is adapted to extend into and through the first and second portions 10, 12 of the bone, respectively, with the central portion 78 disposed along the top surface 26 of the first and second portions 10, 12. The bottom of the right and left portions curling and hooking into the first and second portions 10, 12, respectively, to grip the first and second portions 10, 12.

The present invention pertains to a method for holding a first portion 10 of a bone and a second portion 12 of a bone together for the bone to heal, as shown in FIG. 14. The method comprises the steps of inserting a right portion 84 of a strap made of a memory metal into and through the first portion 10 of the bone and a left portion of the strap into and through the second portion 12 of the bone with a central portion 78 of the strap connecting the right portion 84 and the left portion and extending over and between the first and second portions 10, 12. Then there is the step of heating the right portion 84 and left portion until they curl and the bottom of the right and left portions hook into the first and second portions 10, 12, respectively.

Figure 15:
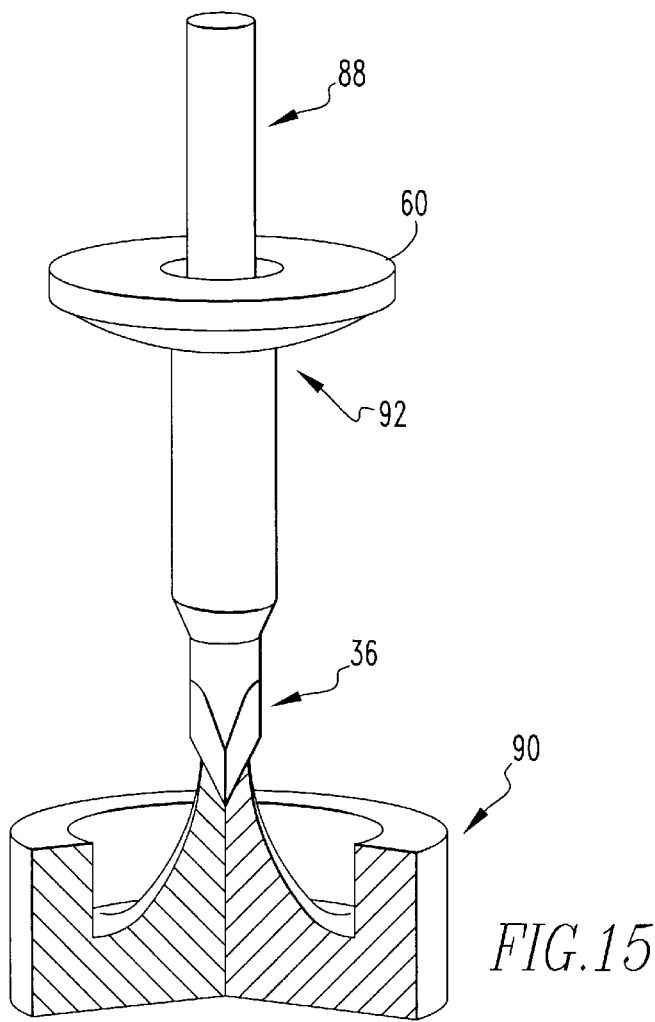
FIG. 15 is a schematic representation of another embodiment of the present invention.
Figure 16:
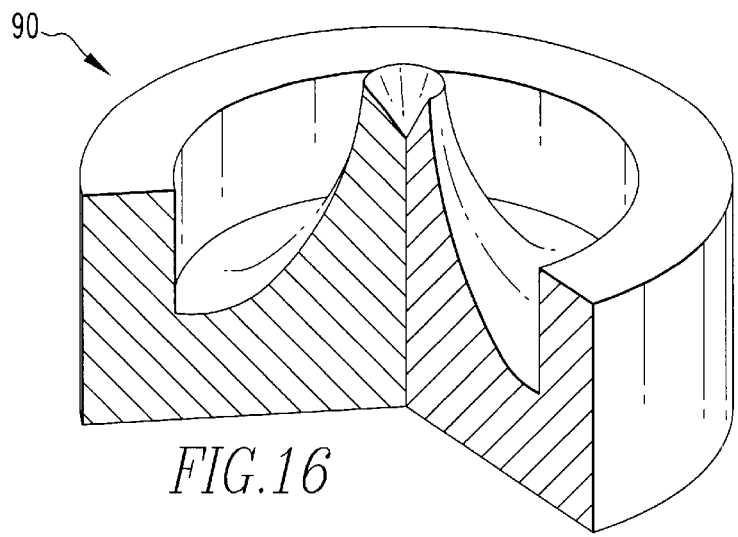
FIG. 16 is a schematic representation of a platform.
Figure 17:
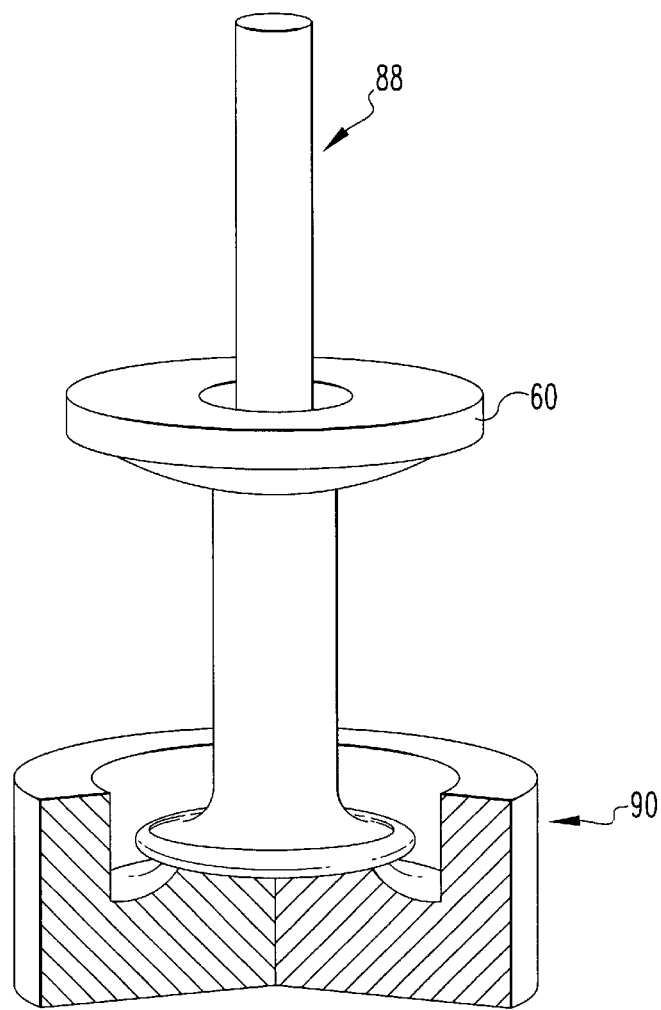
FIG. 17 is a schematic representation of another embodiment of the present invention.

The present invention pertains to an apparatus for holding a first portion 10 of a bone and a second portion 12 of a bone together for the bone to heal, as shown in FIGS. 15, 16 and 17. The apparatus comprises a plurality of grommets, each grommet having a channel, a flange adapted to seat on the surface of the bone, and a tube which extends from the flange and is adapted to be disposed in the bone. The apparatus comprises a suture 18 which extends through at least two of the plurality of grommets which oppose each other when they are disposed in the first and second portions 10, 12 of the bone, respectively. The apparatus comprises a poker 88 which removably fits in the channel of a grommet and has a pointed end adapted to pierce the bone and to install the grommet into the bone. The apparatus comprises a platform against which the tube of one of the grommets with the poker 88 through it is pressed to cause the end of the tube to flare out and form a bottom flange that seats on the bottom surface of the bone.

Figure 18:
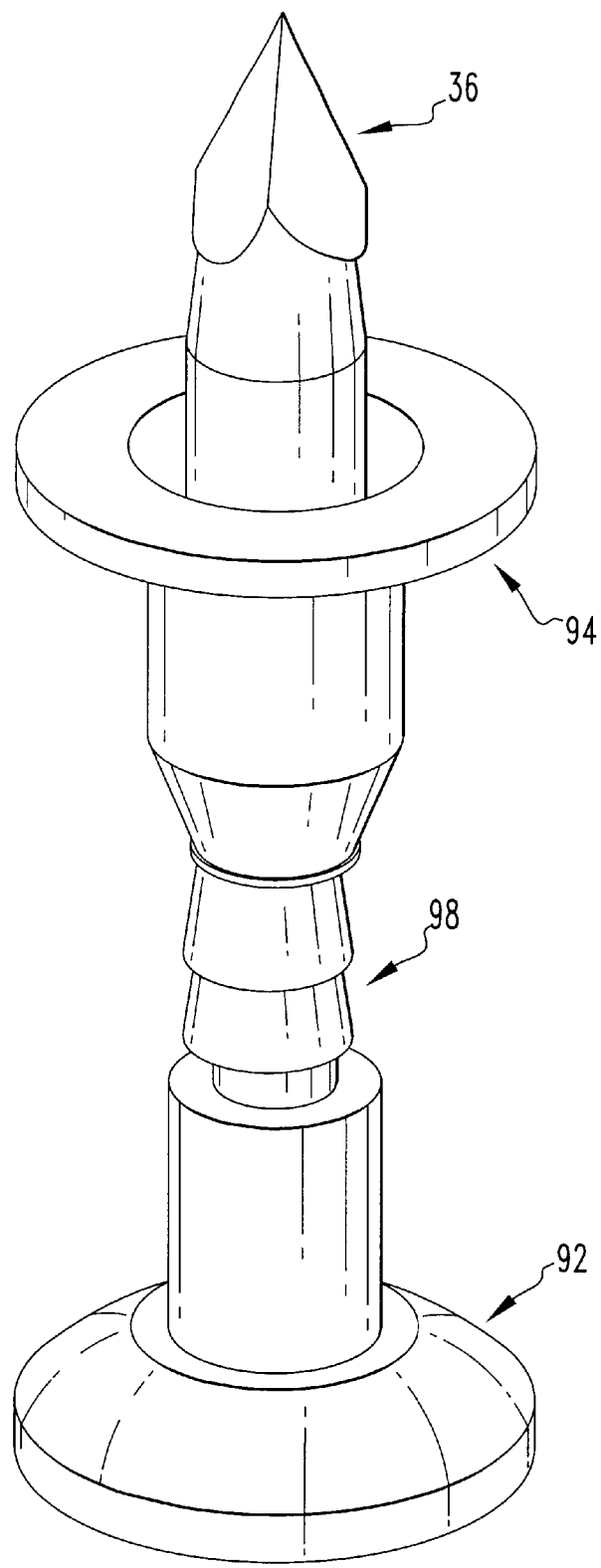
FIG. 18 is a schematic representation of another embodiment of the present invention.
Figure 19:
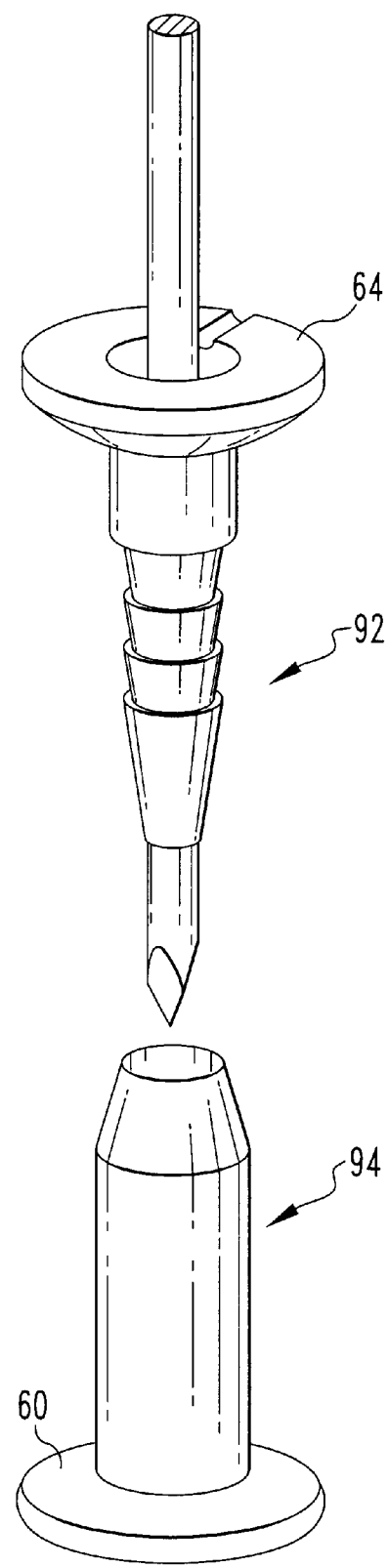
FIG. 19 is a schematic representation of the top portion and bottom portion of the embodiment of FIG. 18 apart.

The present invention pertains to an apparatus for holding a first portion 10 of a bone and a second portion 12 of a bone together for the bone to heal, as shown in FIGS. 18 and 19. The apparatus comprises a plurality of grommets, each having a channel and a top portion 92 and a bottom portion, each portion having a flange adapted to seat on the surface of the bone, and a tube which extends from the flange and is adapted to be disposed in the bone. The apparatus comprises a poker 88 which removably fits in the channel of the top and bottom portions and has a pointed end adapted to pierce the bone and to install the top portion 92 into the bone and along which the bottom portion fits to be guided into the bottom of the bone.

The present invention pertains to a method for holding a first portion 10 of a bone and a second portion 12 of a bone together for the bone to heal, as shown in FIGS. 15, 16 and 17. The method comprises the steps of placing a poker 88 having a pointed end through a channel of a first grommet having a top flange 60 and a tube which extends from the top flange 60. Then there is the step of inserting the poker 88, pointed end first, with the first grommet on it through the top surface 26 of the first portion 10 until it contacts a platform disposed adjacent the bottom surface of the first portion 10 and the tube of the grommet is disposed in and extends through the first portion 10. Next there is the step of pressing the poker 88 against the platform until the bottom of the tube flares out and forms a bottom flange. Then there is the step of removing the poker 88 from the first grommet leaving the first grommet in the first portion 10 with the top flange 60 and bottom flange adjacent to the top surface 26 and bottom surface, respectively. Next there is the step of implanting a second grommet having a channel in the second portion 12. Then there is the step of extending a suture 18 through the channels of the first and second grommets. Next there is the step of bringing the first and second portions 10, 12 together. Next there is the step of securing the first and second portions 10, 12 together with the suture 18.

The present invention pertains to a method for holding a first portion 10 of a bone and a second portion 12 of a bone together for the bone to heal, as shown in FIGS. 18 and 19. The method comprises the steps of placing a poker 88 having a pointed end through a channel of a top portion 92 of a first grommet having a top flange 60 and a tube which extends from the top flange 60. Then there is the step of inserting the poker 88, pointed end first, with the top portion 92 of the first grommet on it through the top surface 26 of the first wherein the flange seats on the top surface 26 of the first portion 10 and the tube is disposed in the first portion 10. Next there is the step of placing a tube of a bottom portion of the first grommet on the pointed end. Then there is the step of sliding the bottom portion along the poker 88 until a flange of the bottom portion seats on the bottom surface of the first portion 10 and the tube of the bottom portion is in the bottom of the first portion 10. Next there is the step of removing the poker 88 from the first grommet leaving the first grommet in the first portion 10 with the top flange 60 and bottom flange seated on the top surface 26 and bottom surface, respectively. Then there is the step of implanting a second grommet having a channel in the second portion 12. Next there is the step of extending a suture 18 through the channels of the first and second grommets. Next there is the step of bringing the first and second portions 10, 12 together. Then there is the step of securing the first and second portions 10, 12 together with the suture 18.

In the operation of the invention, and in regard to a first embodiment thereof, a hole 22 is formed in the first portion of the bone with a drill, and then a hole 22 is formed in a second portion 12 of the bone with the drill, as shown in FIG. 1. A pusher 20 having a shaft with a flange head and an obelisk base, has the base inserted into a first bendable hollow sleeve. The first bendable hollow sleeve is then positioned in the top of the hole 22 in the first portion 10 and force is applied to the flange head, causing the base to move downward into the first hollow sleeve 14 and to move the first hollow sleeve 14 through the first hole 22 as the base moves through the first hollow sleeve 14. Force is applied to the flange head until the first hollow sleeve 14 extends through the first portion 10 of the bone from the top surface 26 to the bottom surface 28 of the first portion 10.

The head is then grabbed and pulled up from the first portion 10 of the bone causing the shaft and base to be pulled back out of the first portion 10 of the first hollow sleeve 14. The friction from the first portion 10 of the first hollow sleeve 14 which is now in the first portion 10, is greater than the fraction of the first hollow sleeve 14 of the base as it moves through the hollow sleeve, resulting in the first hollow sleeve 14 remaining in the first portion 10 while the pusher 20 comes out of the first hollow sleeve 14. This process is repeated with a second hollow sleeve 16 in the second portion 12 of the bone to position the second hollow sleeve 16 in the second portion 12 of the bone adjacent to and opposing the first sleeve 14.

A suture 18 is threaded into and through the first hollow sleeve 14, from the bottom of the first hollow sleeve 14 across to the bottom of the second hollow sleeve 16 in the second portion 12 and into and through the second hollow sleeve 16 until it extends out of the second hollow sleeve 16. The end of the suture 18 extending from the second hollow sleeve 16 is then brought together with the end of the suture 18 extending from the first hollow sleeve 14 and pulled tight, causing the first portion 10 and second portion 12 of the bone to come together. The ends of the suture 18 are then secured together with pliers which is used to twirl the ends around each other and then bend the connected ends downward so they did not extend upwards and interfere with the closing of the skin over the bone in the final steps of the procedure.

Six to eight sets of bendable sleeves are subsequently inserted into the first and second portions 10, 12 of the bone, with a suture 18 extending through each of them and secured together to maintain the length of the sternum together to facilitate healing. Any tissue and skin over the sternum is closed and the operation is completed.

The hollow sleeves serve as insulation 54 to protect the first portion 10 and second portion 12 from tension on the suture 18 that may be created when the patient moves and the healing sternum incurs forces which would cause the first portion 10 and second portion 12 to slide or separate from each other, as shown in FIG. 2. The sleeves absorb and spread out the forces from the sutures 18, which act as the strong structural elements that maintain the first portion 10 and second portion 12 together. Since the sleeves are softer and have a larger in outside diameter than the suture 18, they will not cut into or tear the first portion 10 and second portion 12, especially around the top surface 26 and bottom surface 28 which they extend through and bend about to extend to the opposing portion under any forces that they experience.

In a variation of the aforesaid described embodiment, each bendable hollow sleeve can have a cap on its top which seats on the top surface 26 of the portion of the bone in which the sleeve is inserted, as shown in FIG. 3. In this alternative embodiment, the cap 24 serves to protect the top surface 26 of the bone portion and the bottom of the sleeve bends, as described above to protect the bottom surface 28 of the bone portion. With this embodiment, the bendable hollow sleeve can be designed to be stiff enough so that pressure applied to the cap 24 will force the sleeve into the hole 22, and the sleeve will not bend under the force so that it will penetrate into the hole 22.

In yet another variation of this embodiment, instead of the pusher 20, an implantor 30 is used, as shown in FIG. 4. The implantor 30 has a housing 32 of a cylindrical shape with a groove 34 in which the sleeve fits. The housing 32 also has a pointed end 36 to facilitate insertion through a hole 22 drilled or punched into the bone, or to pierce through the bone if a hole 22 is not already present. When the implantor 30 is used to insert the sleeve into a bone portion, the sleeve is disposed in the groove 34 of the implantor 30 with the suture 18 extending through the sleeve already to provide it stiffness and structural support to aid in maintaining the sleeve with the implantor 30 as it moves through the bone portion. The implantor 30 is pulled back out of the bone portion after the suture 18 is inserted through the sleeve so the bottom of the suture 18 or sleeve can be grabbed and held as the implantor 30 is removed so the implantor 30 does not pull the sleeve upwards and out, or displace the sleeve from the bone portion. Alternatively, the suture 18 can be omitted from the sleeve during the insertion step, and after the sleeve is present in the bone portion, the suture 18 can be inserted, as is described above through the sleeve.

In another embodiment, after a hole 22 is punched or drilled through the first portion 10 and a hole 22 is drilled or punched through the second portion 12 of the bone, a first end 48 of a hollow tube 38 is inserted into the hole 22 in the top surface 26 of the first portion 10, and pushed through the hole 22 in the first portion 10 and out the bottom of the first portion 10 by a way of the hole 22, as shown in FIGS. 5, 6, 7 and 8. The second end 50 of the hollow tube 38 is then inserted into the hole 22 in the top surface 26 of the second portion 12 of the bone. The second end 50 of the hollow tube 38 is pushed through the hole 22 in the second portion 12 and out the bottom of the second portion 12 through the hole 22.

A first end 48 of the suture 18 having a first hollow bottom cap and a second hollow bottom cap threaded on the suture 18 is inserted into the first end 48 of the hollow tube 38 until it extends past the surface of the first portion 10. Similarly, the second end 50 of the suture 18 having the first bottom cap 40 and second bottom cap 42 threaded on it is inserted into the second end 50 of the hollow tube 38 until it extends past the top surface 26 of the second portion 12. The hollow tube 38 is then removed from the suture 18 and the first and second portions 10, 12.

The first bottom cap 40 is then slid along the suture 18 to the bottom surface 28 of the first portion 10 until it reaches the hole 22 in the first portion 10. The first bottom cap 40 is then placed into the bottle surface of the first portion 10 by pushing the cap 24 into the hole 22 so it seats on the bottom surface 28 and extends into the hole 22 of the first portion 10. Similarly, the second bottom cap 42 is slid along the suture 18 to the bottom surface 28 of the second portion 12. The second top cap 46 is then placed into the hole 22 in the bottom surface 28 of the second portion 12 so it seats in the hole 22 and extends into the hole 22 of the second portion 12.

A first top cap 44 is threaded over the first end 48 of the suture 18 and moved along the suture 18 until it comes to the hole 22 in the top surface 26 of the first portion 10. The first top cap 44 is then placed into the hole 22 in the top surface 26 of the first portion 10 by pushing the first top cap 44 into the hole 22 so it seats on the top surface 26 and extends into the hole 22. Similarly, a second top cap 46 is threaded over the second end 50 of the suture 18 and moved along the suture 18 until it reaches the hole 22 in the top surface 26 of the second portion 12. The second top cap 46 is then placed into the hole 22 in the top surface 26 of the second portion 12 by being pushed into the hole 22 so it seats on the top surface 26 and extends into the hole 22. The first and second ends 48, 50 of the suture 18 are then drawn together, causing the first and second portions 10, 12 to move together. The first end 48 and second end 50 of the suture 18 are secured together with pliers by twisting the first and second ends 48, 50 of the suture 18 together to hold the first portion 10 second portion 12 together, as described above.

In a variation of this embodiment, as shown in FIGS. 9–11 and 13, the first and second top caps 44, 46 can be male threaded caps and the first and second bottom caps 40, 42 can be female caps over which the male threaded caps are threaded once they are in place so that the first and second top caps 44, 46 and the first and second bottom caps 40, 42, respectively, are joined together for added stability. This process is repeated for placing the remaining pairs of caps in the first and second portions 10, 12 of the bone. If a hemostat is used to hold the first and second portions 10, 12 of the sternum apart, then the hemostat is removed before the first and second ends 48, 50 of each suture 18 are secured together and the first and second portions 10, 12 of the sternum are closed together.

In another embodiment, a suture 18 comprises a suture 18 adapted to extend through a bone of a patient, as shown in FIG. 2. The suture 18 also comprises an insulation 54 portion disposed about the suture 18 and adapted to protect the bone from the suture 18. The suture 18 having the insulation 54 portion disposed about the suture 18 is threaded through a hole 22 drilled or punched into the first portion 10. The suture 18 that extends out the bottom of the hole 22 in the first portion 10 is then drawn over to a hole 22 in the bottom surface 28 of the second portion 12 of the bone. The suture 18 is threaded through the hole 22 until it extends about the hole 22 in the top surface 26 of the second portion 12. The other end of the suture 18 which extends from the hole 22 in the first portion 10 is then pulled together with the end of the suture 18 which extends out the second portion 12 and secured together, as explained above. Additional sutures 18 are placed in the first and second portions 10, 12 of the bone and secured together in this manner, as needed to secure the first and second portions 10, 12 of the bone together.

In another embodiment, grommets 56 are used to secure a suture 18 through a bone. The grommet 56 comprises a top cap 58 and a bottom cap 62. The top cap 58 has a top flange 60 that is adapted to seat on the top surface 26 of the bone and a threaded portion which extends from the top flange 60 and is adapted to be disposed in the bone. The top flange 60 and threaded portion has a top channel 70 extending through them. The bottom cap 62 has a bottom flange 64 that is adapted to seat on the bottom surface 28 of the bone and a bottom strut 66 which extends from the bottom portion 94 and engages with the threaded portion to hold the top cap 58 into the bottom cap 62 and is adapted to be disposed in the bone. The bottom flange 64 and the strut 66 have a bottom channel 68 extending through them. The top channel 70 and bottom channel 68 are adapted for a suture 18 to extend through the top channel 70 and bottom channel 68.

A hole 22 is drilled or punched into the bone and the bottom of the grommet 56 is inserted into the hole 22 in the bottom surface 28 of the bone so the bottom flange 64 of the bottom cap 62 seats on the bottom surface 28 of the bone and the bottom strut 66 of the bottom cap 62 connecting to the bottom flange 64 extends into the bone. The top cap 58 of the grommet 56 is then placed into the hole 22 in the top surface 26 of the bone so the top flange 60 of the top cap 58 seats on the top surface 26 of the bone and a threaded portion of the top cap 58 connected to the top flange 60 and extends into the bone and contacts the bottom strut 66. The top cap 58 is then rotated, causing the threaded portion of the top cap 58 to screw onto the bottom strut 66. The suture 18 is then inserted through the bone via a channel that extends through the top cap 58 and bottom cap 62.

In another embodiment, as shown in FIG. 12, after holes 22 are punched or drilled into the first portion 10 of the bone and the second portion 12 of the bone, a suture 18 is brought forth to connect the first portion 10 and second portion 12 together. The suture 18 has a first end 48 and a second end 50 with a first needle 72 attached to the first end 48 and a second needle 74 attached to the second end 50. The needles are attached to their respective ends and swedged on them.

The first needle 72 is inserted through a first bottom cap 40 with a flange and the second needle 74 is threaded through a second bottom cap 42 with a flange. The first needle 72 is threaded through the hole 22 in the bottom surface 28 of the first portion 10 and out the hole 22 in the top surface 26 of the first portion 10. The first bottom cap 40 is then guided along the suture 18 until it contacts the hole 22 in the bottom surface 28 of the first portion 10. The first bottom cap 40 is then inserted into the bottom hole 22 of the first portion 10 so it seats on the bottom surface 28 of the first portion 10 with its flange. Similarly, the second needle 74 is threaded through the hole 22 in the second portion 12. The second bottom cap 42 is guided along the suture 18 and inserted into the hole 22 in the bottom of the second portion 12 so the flange seats on the bottom surface 28 of the second portion 12.

The first needle 72 and second needle 74 are then drawn up, causing the suture 18 to tighten between the first hole 22 and the second hole 22. The first needle 72 and second needle 74 are wiggled off of the first end 48 and second end 50, respectively, so they break off the first end 48 and second end 50. A first top cap 44 with a flange is then threaded over the first end 48 of the suture 18 and guided to the hole 22 in the top surface 26 of the first portion 10. The first top cap 44 is then inserted into the hole 22 so the flange of the first portion 10 seats on to the top surface 26 of the first portion 10. Similarly, the second top cap 46 is threaded along the second end 50 of the suture 18 and guided along the suture 18 to the hole 22 in the top surface 26 of the second portion 12. The second top cap 46 is then inserted into a hole 22 on the top surface 26 of the second portion 12 so the flange of the top cap 58 seats on the top surface 26 of the second portion 12. The first end 48 and second end 50 of the suture 18 are them drawn together and secured so the first portion 10 and second portion 12 are brought together and also held in place, as described above. This process is repeated with as many sets of grommets 56 as necessary to securely hold the first portion 10 and second portion 12 together.

If desired, all needle-suture sets can be positioned through opposing holes of the first portion 10 and second portion 12 and only tightened after all of the sets are in place to facilitate the placement of all the sutures 18 without the first portion 10 and second portion 12 being pulled together, making it more difficult for subsequent placement of the grommets 56 and sutures 18 in holes 22 in the first portion 10 and second portion 12.

In another embodiment, as shown in FIG. 14, a strap 76 is used for holding the first portion 10 of the bone and the second portion 12 of the bone together for the bone to heal. The strap 76 is made of a memory metal, such as nitinol. The strap 76 has a central portion 78 with a right side 80 and a left side 82. The strap 76 has a right portion 84 that extends angularly downward from the central portion 78 adjacent to the right portion 84, and a left portion 86 that extends angularly downward from the central portion 78 adjacent to the left side 82. The right and left portion 84, 86 is adapted to extend into and through the first and second portions 10, 12 of the bone, respectively, with the central portion 78 disposed along the top surface 26 of the first and second portions 10,12. The bottom of the right and left portions 84, 86 curl and hook into the first and second portions 10, 12, respectively, to grip the first and second portions 10, 12 when they are heated.

The strap 76 is inserted into place between the first portion 10 and second portion 12 by inserting the right portion 84 of the strap 76 into and through the first portion 10 of the bone and the left portion 86 of the strap 76 into and through the second portion 12 of the bone with a central portion 78 of the strap 76 connecting the right portion 84 and the left portion 86 and extending over and between the first and second portion 10, 12. With the right portion 84 and left portion 86 of the strap 76 disposed in the first portion 10 and second portion 12, respectively, the heat from the first portion 10 and second portion 12 causes the memory metal which makes up the right portion 84 and the left portion 86 to curl and hook into the bottom of the first and second portion 12, respectively. By curling and hooking into the first and second portions 10, 12, the strap 76 seats itself into the bone and holds the first portion 10 and second portion 12 together.

In another embodiment, as shown in FIGS. 15, 16 and 17, a poker 88 having a pointed end 36 is placed through a channel of a first grommet 56 having a top flange 60 and a tube which extends from the top flange 60. The poker 88, pointed end 36 first, with the first grommet 56, is inserted through the top surface 26 of the first portion 10 until it contacts a platform 90 disposed adjacent to the bottom surface 28 of the first portion 10 and the tube of the grommet 56 is disposed in and extends through the first portion 10. The poker 88 is pressed against the platform 90 until the bottom of the tube flares out and forms a bottom flange 64. The poker 88 is removed from the first grommet 56 which leaves the first grommet 56 in the first portion 10 due to the bottom flange 64 preventing the first grommet 56 from pulling out with the poker 88. The top flange 60 of the grommet 56 is seated on the top surface 26 and the bottom flange 64 is seated on the bottom surface 28.

The second grommet 56 is similarly inserted in the second portion 12 opposing the first grommet 56. A suture 18 is threaded through the channels of the first and second grommets. The first and second ends 48, 50 of the suture 18 are pulled together to bring the first portion 10 and second portion 12 together. The first and second ends 48, 50 of the suture 18 are then secured together to maintain the first and second portions 10, 12 together, as described above.

In another embodiment, as shown in FIGS. 18 and 19, a poker 88 having a pointed end 36 is placed through a channel of a top portion 92 of a first grommet 56 having a top flange 60 in a tube which extends from the top flange 60. The poker 88, pointed end 36 first, with the top portion 92 of the first grommet 56 on it, is inserted through the top surface 26 of the first portion 10 so the flange seats on the top surface 26 of the first portion 10 and the tube is disposed in the first portion 10. A tube of a bottom portion 94 of the first grommet 56 is placed on the pointed end 36 of the poker 88. The bottom portion 94 is slid along the poker 88 until a flange of the bottom portion 94 seats on the bottom surface 28 of the first portion 10 and the tube of the bottom portion 94 is in the bottom of the first portion 10. The poker 88 is removed from the first grommet 56 leaving the first grommet 56 in the first portion 10 with the top flange 60 and bottom flange 64 seated on the top surface 26 and bottom surface 28, respectively.

A second grommet 56 is then implanted in the second portion 12 in a similar manner as the first grommet 56 is inserted in the first portion 10. A suture 18 is then threaded through the channels of the first and second grommet 56. The ends of the suture 18 are then pulled together to bring the first and second portions 10, 12 together. The first and second ends 48, 50 of the suture 18 are then secured together to secure the first and second portions 10, 12 together, as described above.

Figure 21:
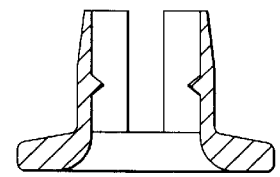
FIG. 21 is a schematic representation of a top view of the embodiment of FIG. 20.
Figure 20:
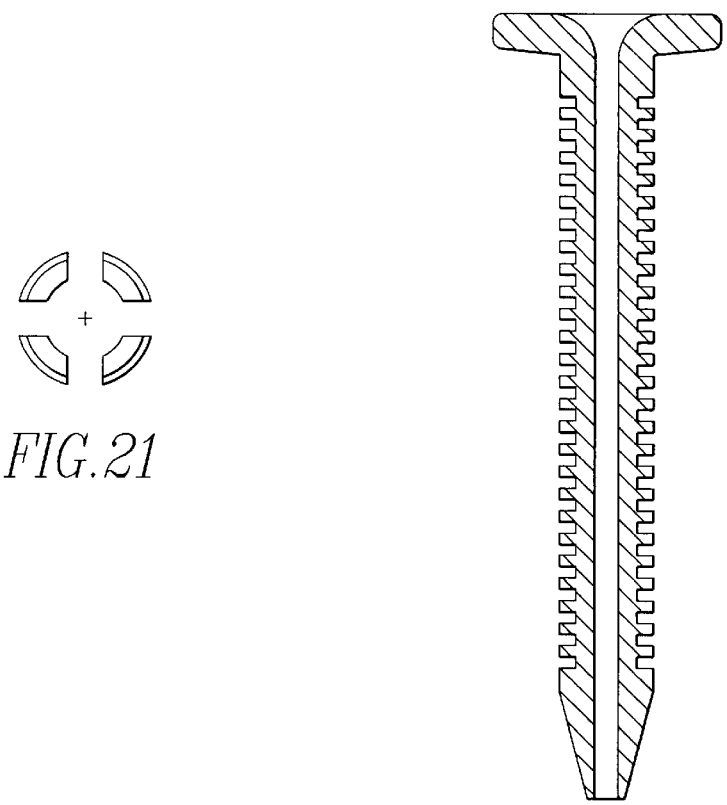
FIG. 20 is a schematic representation of a side view of another embodiment of the present invention.

The present invention pertains to a grommet 56 for a bone, as shown in FIGS. 20 and 21. The grommet 56 comprises a top cap 58 having a top flange 60 adapted for placement on the top surface of the bone and a top strut adapted for placement in the bone extending from the top flange 60, the top strut having slots 97 disposed along its outer surface. The top cap 58 has a channel for a suture 18 to extend through. The top strut 93 is adapted for placement in the bone. The grommet 56 comprises a bottom cap 62 having a bottom flange 64 adapted for placement on the bottom surface of the bone and a bottom strut 95 adapted for placement in the bone extending from the bottom flange 64. The bottom strut 95 has a catch 98 extending from its inner surface to engage a slot 97 to secure the top cap 58 and bottom cap 62 together.

The present invention pertains to a method for holding a first portion 10 of a bone and a second portion 12 of a bone together for the bone to heal, as shown in FIGS. 20 and 21. The method comprises the steps of inserting a top strut 93 of a top cap 58 of a first grommet 56 into a hole in the top surface of the first portion 10 until a top flange 60 of the top cap 58 seats on the top surface of the bone. Then there is the step of inserting a bottom strut 95 of a bottom cap 62 of the first grommet 56 into the hole in the bottom surface of the first portion 10 until a catch 98 extending from the inner surface of the bottom strut of engages a slot 97 disposed along the outer surface of the top strut wherein the top cap 58 and bottom cap. 62 are secured together. Next there is the step of inserting a second grommet 56 having a channel into a second portion 12 of the bone. Then there is the step of threading a suture 18 through a channel of the first grommet 56 and the channel of the second grommet 56. Next there is the step of pulling the first portion 10 and the second portion 12 together. Then there is the step of securing the suture 18 wherein the first portion 10 and second portion 12 are secured together.

Figure 22:
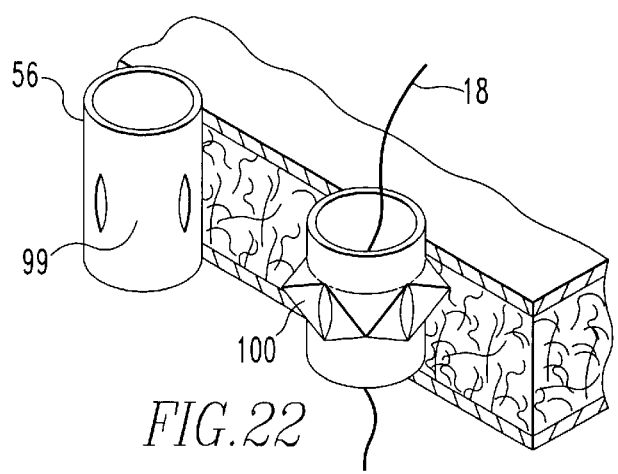
FIG. 22 is a schematic representation of another embodiment of the present invention.

The present invention pertains to a grommet 56 for insertion in a bone, as shown in FIG. 22. The grommet 56 comprises a housing 32 having a channel for a suture 18. The housing 32 is adapted for placement in the bone. The housing 32 has at least one pre-crimp 99 in its wall which expands outward and collapses to form an anchor 100 in the bone when the housing 32 is compressed in an axial direction.

The present invention pertains to a method for placing a suture 18 through a bone, as shown in FIG. 22. The method comprises the steps of inserting a grommet 56 into a bone. Then there is the step of compressing the grommet 56 axially from its top and bottom causing a pre-crimp 99 in the housing wall to extend outward and collapse to form an anchor 100 in the bone Next there is the step of threading a suture 18 through a channel in the grommet 56.

The present invention pertains to a grommet for implantation into a hole in hard or soft tissue of a patient. The grommet comprises a spring having a head flange adapted to seat on the top portion of the tissue. The grommet comprises a tail flange adapted to seat on the top portion of the tissue. The grommet comprises an elongate central portion connected to the head flange and the tail flange. Preferably, the tail flange has a tail end which bends inwards.

Figure 23:
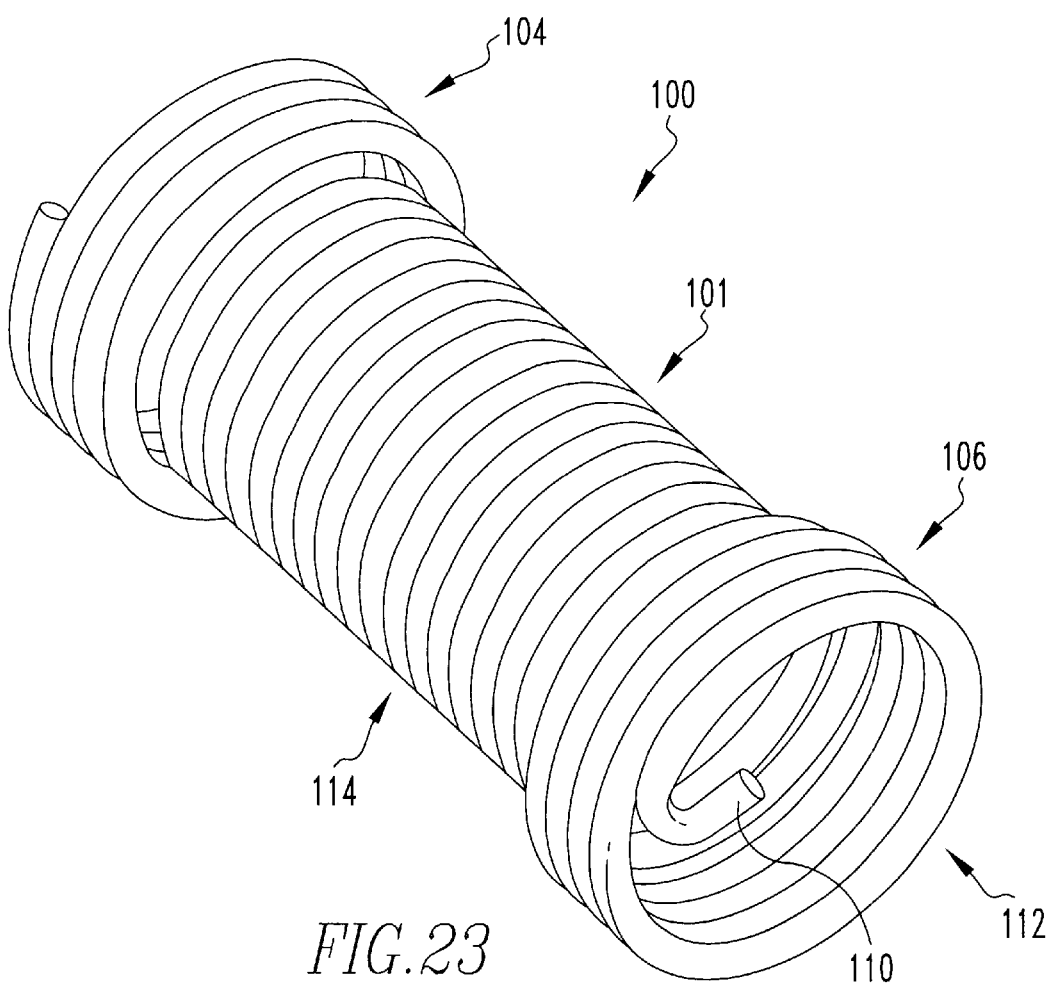
FIG. 23 is a schematic representation of a grommet in the form of a spring.
Figure 24:
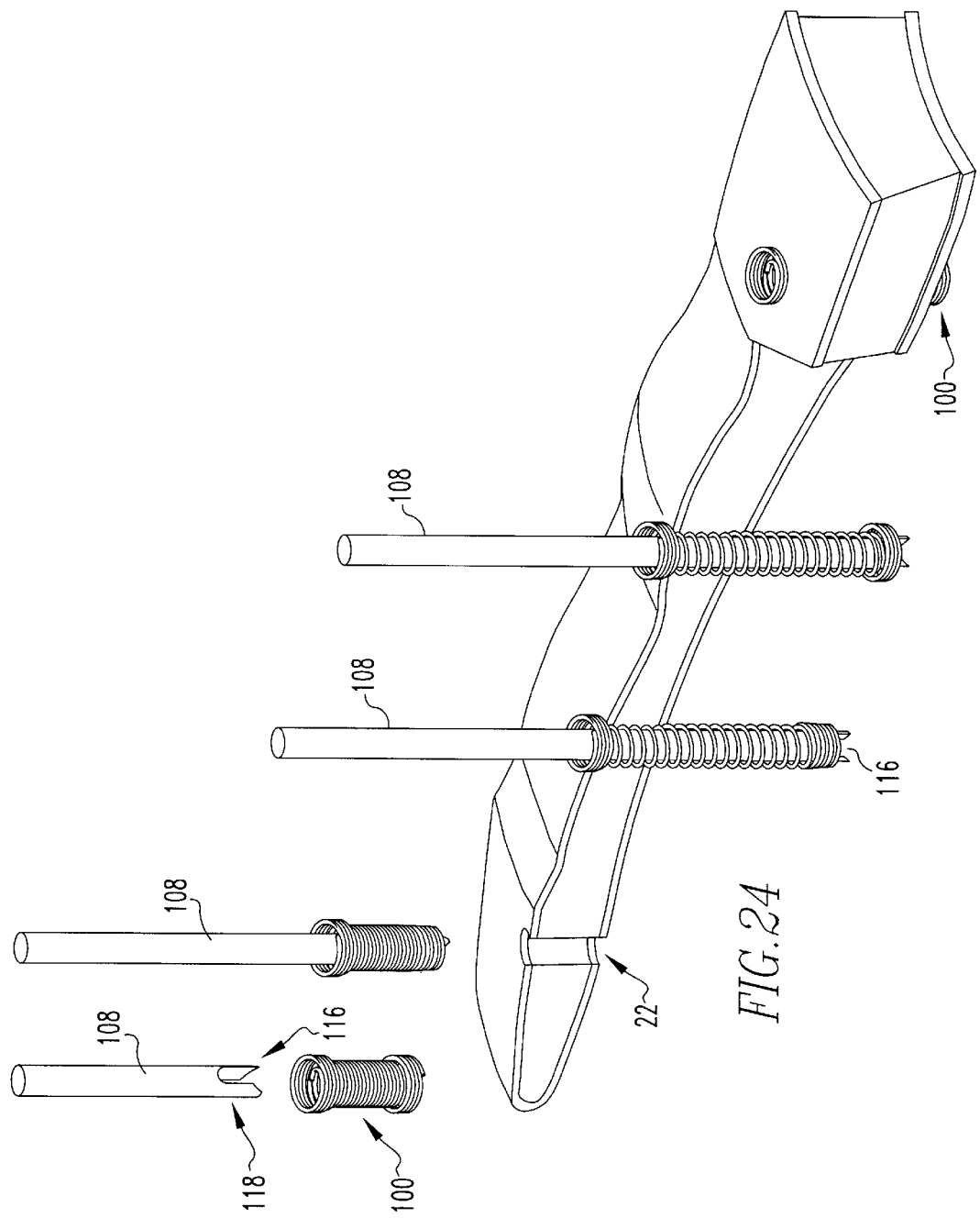
FIG. 24 is a schematic representation of grommets in the form of a spring being inserted into tissue.
Figure 25:
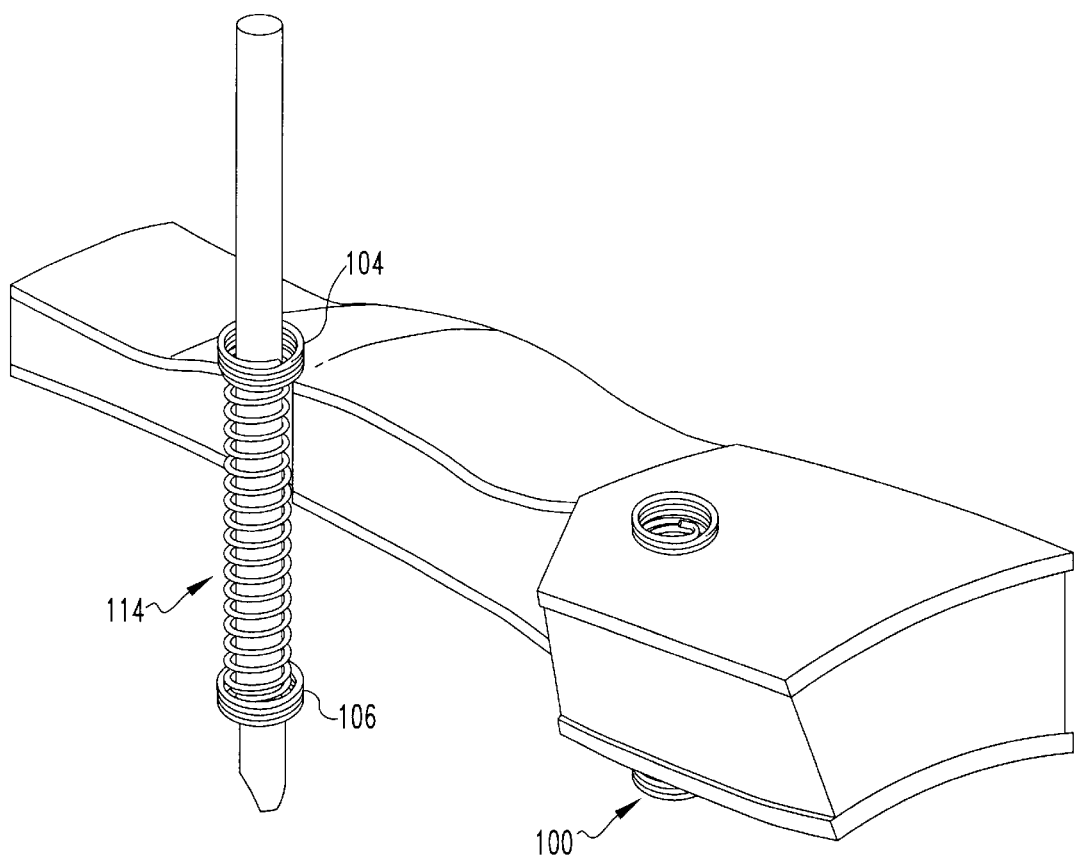
FIG. 25 is a schematic representation of a grommet in the form of a spring inserted into tissue.

In another embodiment, a grommet 100 is formed from a wire wound into a spiral, much in the form of a spring 101. As shown in FIGS. 23, 24 and 25, the spring 101 is wound to form a head flange 104 having a diameter greater than the diameter of the hole 22 in the bone in which it is to be inserted. The spring 101 is wound to form a tale flange 106 having a diameter greater than the diameter of the hole 22 in the bone in which it is to be inserted. The tail end 110 of the spring 101 at the tail flange 106 of the grommet 100 bends slightly inwards from its circumference. The spring 101 has a channel 112 through which a wire suture 18 extends when the grommet 100 is in place. There is also an elongated central portion 114 connected between the head flange 104 and the tail flange 106 which has an outer diameter slightly larger than the diameter of the hole 22 in the bone in which it is to be inserted.

A pushing rod 108 has a diameter smaller than the inner diameter of the channel 112 of the grommet 100 and has a slot 116 in its pushing end 118. To place the grommet 100 into the hole 22 in the bone, the slot 116 of the pushing rod 108 is inserted into the channel 112 of the grommet 100 and moved through the channel 112 of the grommet 100 until the slot 116 fits over the tail end 110 of the spring 101 which bends slightly inwards. Once the slot 116 grasps the end of the spring 101, the pushing rod 108 is twisted while the head flange 104 of the grommet 100 is held, causing the tail flange 106 and the central portion 114 to narrow in diameter as the length of the grommet 100 extends under the twisting action. With the outer diameter of the tail flange 106 and the central portion 114 now smaller than the inner diameter of the hole 22 in the bone, the tail flange 106 and central portion 114 is inserted with the pushing rod 108 into the hole 22 in the bone until the tail flange 106 extends beyond the bottom of the hole 22 in the bone.

Figure 26:
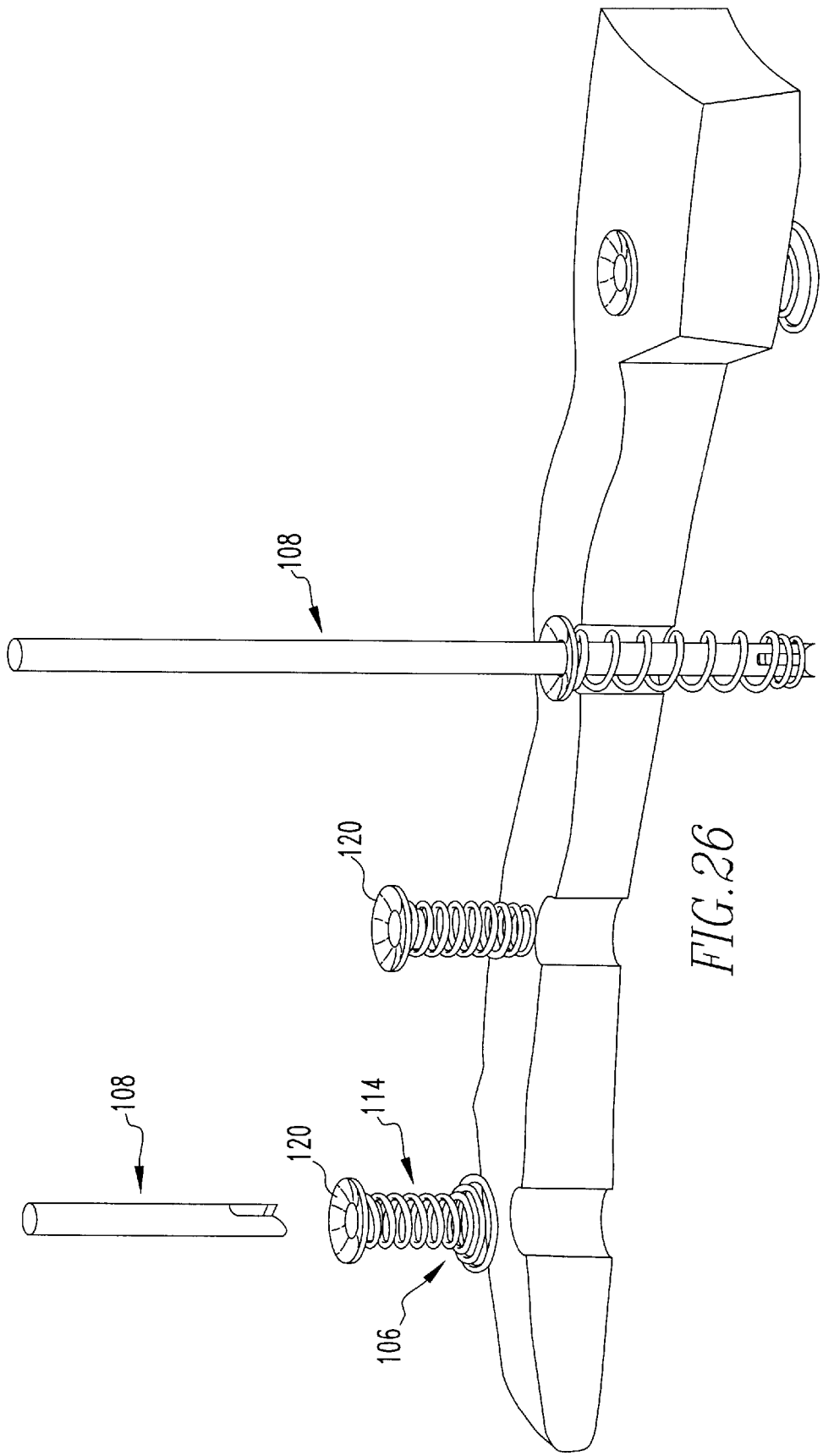
FIG. 26 is a schematic representation of an alternative embodiment of grommets in the form of a spring being inserted into tissue.

The pushing rod 108 is then backed out of the grommet 100 and the hole 22, resulting in the release of tension on the tail flange 106 portion and the central portion 114. When the tail flange 106 and the central portion 114 relaxes from the release of tension, the tail flange 106 expands to its normal diameter, as does the central portion 114. The grommet 100, now in place in the bone, cannot be removed from the bone without considerable damage to the bone since the tail flange 106 and in the head flange 104 extend beyond the diameter of the hole 22, and the central portion 114 forms a friction fit with the inner diameter of the hole 22. The head flange 104 and the tail flange 106 also serve to protect the top and bottom surface of the bone, respectively, from any abrasion or tear due to forces from a wire suture 18 pressing against the bone after the wire suture 18 has been threaded through the grommet 100 and the bone. As described above, additional grommets 100 are inserted into the first and second portions of bone of the patient, and the first and second portions brought together and secured. In an alternative embodiment, as shown in FIG. 26, the head flange 104 instead has a solid flange 120. Standard manufacturing techniques are used to produce the grommet 100.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for holding a first portion of a bone and a second portion of a bone together for the bone to heal comprising:

a first bendable hollow sleeve adapted for insertion into the first portion of the bone;

a second bendable hollow sleeve adapted for insertion into a second portion of the bone;

a suture which is threaded through the first and second sleeves; and a pusher for pushing the first and second sleeves into the first and second portions of the bone, respectively, wherein when the suture is tightened, the first and second portions are pulled together and the first and second sleeves bend and protect the first and second portions from the suture.

2. A method for holding a first portion of a bone and a second portion of a bone together for the bone to heal comprising the steps of:

inserting a first bendable hollow sleeve into the first portion of the bone;

inserting a second bendable hollow sleeve into the second portion of the bone;

threading a suture through the first and second sleeves; and pulling the first portion and second portion together with the suture and causing the first and second sleeves to bend and protect the first and second portions from the suture contacting the first and second portions.

3. A method as described in claim 2 including after the pulling step, there is the step of closing the first and second ends of the suture together.

4. A method as described in claim 3 wherein the first sleeve inserting step includes the step of placing a pusher in the first sleeve, pushing the first sleeve through the first portion with the pusher, and removing the pusher from the first sleeve.

5. A method as described in claim 4 wherein the second sleeve inserting step includes the step of placing the pusher in the second sleeve, pushing the second sleeve through the second portion with the pusher, and removing the pusher from the second sleeve.

6. A method as described in claim 5 wherein before the inserting the first sleeve step, there is the step of forming a hole through the first portion.

7. A method as described in claim 6 wherein before the inserting the second sleeve step, there is the step of forming a hole through the second portion.

8. A method as described in claim 2 wherein after the first sleeve inserting step, there is the step of seating a cap of the first sleeve on the top surface of the first portion and after the second sleeve inserting step, there is the step of seating a cap of the second sleeve on a top surface of the second portion.

9. A method as described in claim 2 wherein the inserting the first sleeve step includes the step of inserting an implantor in which the first sleeve is disposed into the first portion and wherein the inserting the second sleeve step includes the step of inserting the implantor in which the second sleeve is disposed into the second portion.

10. A method as described in claim 9 wherein before the first sleeve inserting step, there is the step of placing the first sleeve with the implantor.

11. An apparatus for holding a first portion of a bone and a second portion of a bone together for the bone to heal comprising:

a first bendable hollow sleeve adapted for insertion into the first portion of the bone;

a second bendable hollow sleeve adapted for insertion into a second portion of the bone;

a suture which is threaded through the first and second sleeves; and an implantor which holds the first or second sleeve and inserts the first or second sleeve into the first or second portion, respectively.

12. An apparatus as described in claim 10 wherein the implantor has a housing of a cylindrical shape with a groove in which the first or second sleeve fits, and with a pointed end.

* * * * *